United States Patent
Tajima et al.

(10) Patent No.: US 9,780,128 B2
(45) Date of Patent: Oct. 3, 2017

(54) RADIATION IMAGE DETECTING DEVICE, RADIATION IMAGING SYSTEM AND OPERATION METHOD THEREOF

(71) Applicant: FUJIFILM Corporation, Tokyo (JP)

(72) Inventors: Takashi Tajima, Ashigarakami-gun (JP); Takeshi Kuwabara, Ashigarakami-gun (JP); Yusuke Kitagawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 446 days.

(21) Appl. No.: 14/604,352

(22) Filed: Jan. 23, 2015

(65) Prior Publication Data

US 2015/0131784 A1 May 14, 2015

Related U.S. Application Data

(63) Continuation of application No. PCT/JP2013/065669, filed on Jun. 6, 2013.

(30) Foreign Application Priority Data

Jul. 27, 2012 (JP) ................................ 2012-166876
May 23, 2013 (JP) ................................ 2013-109301

(51) Int. Cl.
*G01T 1/02* (2006.01)
*H05G 1/44* (2006.01)
(Continued)

(52) U.S. Cl.
CPC ...... *H01L 27/14603* (2013.01); *A61B 6/4291* (2013.01); *A61B 6/542* (2013.01);
(Continued)

(58) Field of Classification Search
CPC ....... A61B 6/42; A61B 6/4208; A61B 6/4283; A61B 6/4291; A61B 6/44; A61B 6/48;
(Continued)

(56) References Cited

U.S. PATENT DOCUMENTS 6,944,266 B2    9/2005 Yamazaki et al.

FOREIGN PATENT DOCUMENTS

| CN | 102656478 A | 9/2012 |
| JP | 7-201490 A | 8/1995 |
| JP | 2004-166724 A | 6/2004 |

OTHER PUBLICATIONS

Chinese Office Action issued Aug. 25, 2016 in counterpart CN Application No. 201380045149.5 with an English Translation.
(Continued)

*Primary Examiner* — Anastasia Midkiff
(74) *Attorney, Agent, or Firm* — Birch, Stewart, Kolasch & Birch, LLP

(57) ABSTRACT

An image detector is disposed behind a grid. The image detector has normal pixels and measurement pixels. Out of a group of measurement pixels based on which an average value of dose measurement signals is calculated, a [C/D] number of measurement pixels are disposed or chosen in a cycle $Z=(R \times C) \pm D$. Wherein, C represents a cycle of a repetition pattern appearing in an arrangement direction of X-ray transparent layers and X-ray absorbing layers in an X-ray image of the grid, and is represented in units of the number of pixels. R represents a natural number of 0 or more. D represents an integer less than the cycle C. [C/D] represents a maximum integer equal to or less than C/D. Provided that at least the [C/D] number of measurement pixels are shifted C occasions by one pixel, if D=1, the average value of the dose measurement signals is invariable without any variations.

16 Claims, 14 Drawing Sheets

(51) Int. Cl.
  *H05G 1/42* (2006.01)
  *H05G 1/38* (2006.01)
  *H05G 1/28* (2006.01)
  *H01L 27/146* (2006.01)
  *H01L 27/148* (2006.01)
  *G01T 1/16* (2006.01)
  *H01L 27/144* (2006.01)
  *A61B 6/00* (2006.01)

(52) U.S. Cl.
  CPC .............. *A61B 6/585* (2013.01); *G01T 1/026* (2013.01); *G01T 1/1603* (2013.01); *H01L 27/14812* (2013.01); *H05G 1/28* (2013.01); *H05G 1/38* (2013.01); *H05G 1/42* (2013.01); *H05G 1/44* (2013.01); *A61B 6/4233* (2013.01); *A61B 6/4452* (2013.01); *H01L 27/1446* (2013.01); *H01L 27/14658* (2013.01)

(58) Field of Classification Search
  CPC ........... A61B 6/488; A61B 6/54; A61B 6/542; A61B 6/545; A61B 2562/00; A61B 2562/02; A61B 2562/06; A61B 2562/066; G01T 1/00; G01T 1/02; G01T 1/026; G01T 1/16; G01T 1/1603; G01T 1/24; G01T 1/246; G01T 1/247; H01L 27/1446; H01L 27/146; H01L 27/14601; H01L 27/14603; H01L 27/14609; H01L 27/14625; H01L 27/14658; H01L 27/14676; H01L 27/148; H01L 27/14806; H01L 27/14812; H05G 1/00; H05G 1/08; H05G 1/26; H05G 1/28; H05G 1/30; H05G 1/38; H05G 1/42; H05G 1/44; G05F 5/00; G05B 1/00; G05B 1/01; G05B 1/03; G05B 6/00; G05B 6/02; G05B 21/00; G05B 21/02; G05B 2219/15097
  See application file for complete search history.

(56) References Cited

OTHER PUBLICATIONS

International Search Report, issued in PCT/JP2013/065669, dated Sep. 10, 2013.
Written Opinion of the International Searching Authority, issued in PCT/JP2013/065669, dated Sep. 10, 2013.

FIG. 11

DOSE MEASUREMENT SIGNAL OF OUTPUT PATTERN "HIGH" = 1
DOSE MEASUREMENT SIGNAL OF OUTPUT PATTERN "LOW" = 0.9

| NUMBER OF MEASUREMENT PIXELS | OUTPUT PATTERN | SUM VALUE | AVERAGE VALUE |
|---|---|---|---|
| 2 | H, H | 2 | 1 |
| | H, L | 1.9 | 0.95 |
| | L, L | 1.8 | 0.9 |
| 3 | H, H, H | 3 | 1 |
| | H, H, L | 2.9 | 0.967 |
| | H, L, L | 2.8 | 0.933 |
| | L, L, L | 2.7 | 0.9 |
| 4 | H, H, H, H | 4 | 1 |
| | H, H, H, L | 3.9 | 0.975 |
| | H, H, L, L | 3.8 | 0.95 |
| | H, L, L, L | 3.7 | 0.925 |
| | L, L, L, L | 3.6 | 0.9 |
| ⋮ | ⋮ | ⋮ | ⋮ |

FIG. 12

| NUMBER OF MEASUREMENT PIXELS | MAXIMUM VALUE | MINIMUM VALUE | MAXIMUM VALUE / MINIMUM VALUE | JUDGMENT |
|---|---|---|---|---|
| 2 | 1 | 0.95 | 1.05 | OK |
|  | 1 | 0.9 | 1.11 | NG |
|  | 0.95 | 0.9 | 1.06 | OK |
| 3 | 1 | 0.967 | 1.03 | OK |
|  | 1 | 0.933 | 1.07 | OK |
|  | 1 | 0.9 | 1.11 | NG |
|  | 0.967 | 0.933 | 1.04 | OK |
|  | 0.967 | 0.9 | 1.07 | OK |
|  | 0.933 | 0.9 | 1.04 | OK |
| 4 | 1 | 0.975 | 1.03 | OK |
|  | 1 | 0.95 | 1.05 | OK |
|  | 1 | 0.925 | 1.08 | OK |
|  | 1 | 0.9 | 1.11 | NG |
|  | 0.975 | 0.95 | 1.03 | OK |
|  | 0.975 | 0.925 | 1.05 | OK |
|  | 0.975 | 0.9 | 1.08 | OK |
|  | 0.95 | 0.925 | 1.03 | OK |
|  | 0.95 | 0.9 | 1.06 | OK |
|  | 0.925 | 0.9 | 1.03 | OK |
| ⋮ | ⋮ | ⋮ | ⋮ | ⋮ |

RADIATION IMAGE DETECTING DEVICE, RADIATION IMAGING SYSTEM AND OPERATION METHOD THEREOF

CROSS-REFERENCE TO RELATED APPLICATIONS

This application is a continuation of PCT International Application No. PCT/JP2013/065669 filed on Jun. 6, 2013, which claims priority under 35 U.S.C. 35 §119(a) to Japanese Patent Application No. 2012-166876 filed on Jul. 27, 2012 and Japanese Patent Application No. 2013-109301 filed on May 23, 2013. Each of the above applications is hereby expressly incorporated by reference, in its entirety, into the present application.

BACKGROUND OF THE INVENTION

1. Field of the Invention

The present invention relates to a radiation image detecting device for detecting a radiographic image through a grid, a radiation imaging system and an operation method thereof.

2. Description Related to the Prior Art

In a medical field, a radiation imaging system, for example, an X-ray imaging system using X-rays is known. The X-ray imaging system is constituted of an X-ray generating apparatus for producing the X-rays, and an X-ray imaging apparatus for taking an X-ray image formed by the X-rays passed through an object (a patient). The X-ray generating apparatus has an X-ray source for emitting the X-rays to the object, a source control device for controlling the operation of the X-ray source, and an emission switch for commanding the source control device to start X-ray emission. The X-ray imaging apparatus has an X-ray image detecting device for detecting the X-ray image by converting the X-rays passed through each part of the object into an electric signal, and a console for controlling the operation of the X-ray image detecting device and saving and displaying the X-ray image.

The X-ray image detecting device includes an image detector for converting the X-ray image into the electric signal, a controller for controlling the image detector, and the like. As the image detector, a flat panel detector (FPD) having a lot of pixels arrayed in two dimensions in an imaging area is widely used. Each pixel accumulates electric charge in accordance with an X-ray dose (a time-integrated X-ray value). After imaging, the electric charge accumulated in each pixel is read out to a signal processing circuit through a switching element such as a TFT (thin film transistor). The signal processing circuit converts the electric charge of each pixel into a voltage signal, and outputs the voltage signals as an X-ray image signal.

There is known an X-ray image detecting device that has an X-ray dose measurement function and an automatic exposure control (AEC) function (for example, Japanese Patent Laid-Open Publication No. 07-201490). In this X-ray image detecting device, one or a plurality of measurement pixels for measuring an X-ray dose is disposed in the imaging area of the image detector, together with normal pixels (X-ray image detection pixels) for detecting an X-ray image. This measurement pixel is used as a dose measurement sensor for measuring the X-ray dose. A measurement signal is read out of the measurement pixel at regular time intervals and integrated to measure the X-ray dose. At the instant when the X-ray dose reaches a predetermined emission stop threshold value (a target X-ray dose) the AEC function commands the X-ray source to stop X-ray emission. In the following description, both of the normal pixels and the measurement pixels are collectively called pixels. The pixel refers to an ingredient that has at least a conversion function for converting a small portion of the X-ray image into the electric charge.

The measurement pixel is the same as or several times larger than the normal pixel in size, and is disposed in one or a plurality of portions in the imaging area. Provided that the measurement pixel is the same size as the normal pixel, the normal pixel may be substituted with the measurement pixel or changed into the measurement pixel by easy modification. In some cases, the normal pixel may be used as the measurement pixel, or variation in a leak current or a bias current of the normal pixel may be detected to measure the X-ray dose therefrom. The small-sized measurement pixel does not hinder the detection of the X-ray image and hence facilitate detecting the X-ray image with high resolution, as compared with a conventional large-sized dose measurement sensor such as an ion chamber. Furthermore, selective use of the measurement pixels in accordance with a body part to be imaged makes it possible to precisely measure the X-ray dose passed through the body part.

By the way, in X-ray imaging, the X-rays produce scattered radiation in passing through the object. To remove this scattered radiation, a thin plate-shaped grid is used often. This grid is disposed between the object and the X-ray image detecting device, and preferably just in front of the X-ray image detecting device. There are two types of grids, one known as a movable grid swinging during X-ray imaging and the other known as a static grid standing still. In the following description, either type of grid is simply called grid except in cases where distinction between the types is necessary.

The grid is provided with strip-shaped X-ray transparent layers and X-ray absorbing layers that extend in a column direction of the pixels and are alternately and repeatedly arranged along a row direction of the pixels. Since the X-ray absorbing layer absorbs the X-rays passed through the object, widening the X-ray absorbing layers deteriorates the image quality of the X-ray image to be taken. Accordingly, the width of the X-ray absorbing layer is, for example, of the order of $1/5$ to $1/3$ of the width of the X-ray transparent layer, in general.

According to X-ray imaging using the grid, since the X-ray absorbing layers of the grid attenuate the X-rays to be incident upon the measurement pixels, a measurement value of each measurement pixel has to be calibrated to measure an X-ray irradiation amount (an X-ray exposure amount) of the object. This calibration method of the measurement value is described in U.S. Pat. No. 6,944,266 corresponding to Japanese Patent Laid-Open Publication No. 2004-166724, for example. First, the X-ray imaging is performed in a state of disposing no object with and without using the grid. From two images obtained thereby, a correction coefficient of each individual measurement pixel is calculated such that an output signal of the measurement pixel (referred to as an AEC pixel in the U.S. Pat. No. 6,944,266) becomes the same between with and without the grid. In imaging using the grid, the output signal of the measurement pixel is multiplied by the correction coefficient to calibrate the X-ray dose.

An arrangement direction of the X-ray transparent layers and the X-ray absorbing layers of the grid is orthogonal to a row direction of the pixels. Provided that the normal pixel and the measurement pixel are of the same size, the size of one normal pixel (the pitch of the pixels) is 100 μm to 200 μm, and hence the size of the measurement pixel is of the order of 100 μm to 200 μm. On the other hand, there are two types of grids in which the number of the X-ray absorbing layers per unit length in the arrangement direction is 100/cm and 32/cm. By converting this number into a grid pitch (an arrangement pitch of the X-ray absorbing layers), grid pitches of 100 μm and approximately 300 μm are obtained.

Taking the case of a grid pitch of 300 μm and a measurement pixel size of 100 μm as an example, since the width of the X-ray absorbing layers is approximately 50 μm to 100 μm, a shift of the positional relation between the grid and the measurement pixels changes overlap between the measurement pixels and the X-ray absorbing layers and hence largely varies the output signals.

Since the X-ray transparent layers and the X-ray absorbing layers are regularly arranged at a constant period in the grid, an M or M+1 (M is an integer of 0 or more) number of X-ray absorbing layers are opposed to an arbitrary measurement pixel in accordance with the relation between the grid pitch and the size of the measurement pixels. Thus, in a case where the positional relation between the grid and the measurement pixels is shifted, variation in the output signal of the measurement pixel has its maximum value that corresponds to attenuation of the X-rays absorbed by one X-ray absorbing layer relative to the measurement pixel. Given that each X-ray absorbing layer has an almost constant X-ray absorptivity, the variation in the output signal is increased with decrease in the number M. If the grid pitch takes a value close to the size of the measurement pixels, the number M is a relatively small value. Therefore, the output signal of the measurement pixel is especially susceptible to the X-ray absorbing layer, and a problem of measurement precision of the X-ray dose owing to the shift of the positional relation between the grid and the measurement pixels becomes conspicuous.

The effect of the X-ray absorbing layers can be calculated from an image of the stopped movable grid or the still grid captured in the absence of the object. According to experiment of the inventors, it is apparent that a pixel value is decreased on the order of 20% by a certain grid owing to the effect of the X-ray absorbing layer, by comparison between a large pixel value and a nearby decreased pixel value that the X-ray absorbing layer affects.

In a case where the grid is secured to the X-ray image detecting device, variations in attachment position of each part in manufacturing cause the shift of the positional relation between the grid and the measurement pixels. In the case of an electronic cassette separate from the grid or in the case of the grid detachable from an imaging stand or an imaging table, variations in loading position of the electronic cassette or the grid cause the shift of the positional relation between the grid and the measurement pixels. In some cases, the positional relation between the grid and the measurement pixels may be shifted by vibration and the like while imaging is repeatedly performed.

According to the U.S. Pat. No. 6,944,266, in a case where the positional relation between the grid and the measurement pixels is shifted whenever imaging is performed, a lot of calibration images are prepared in accordance with a shift amount, and the shift amount is detected in imaging on the order of μm corresponding to the grid pitch. One of the calibration images is chosen in accordance with the shift amount, and the correction coefficient to correct sensitivity of the measurement pixel is calculated. This calibration method of the measurement pixels precisely measures the shift amount and allows calibration with high precision, but requires the many calibration images. Also, in a case where the positional relation between the grid and the measurement pixels is shifted during manufacturing, the calibration images have to be taken on a product-by-product basis, and its preparation operation requires much time and effort. Furthermore, a huge number of calibration images have to be prepared at the thought of oblique incidence of the X-rays upon the imaging area, so that realization is difficult. Accordingly, it is desired that the X-ray dose can be measured easily and precisely even if the positional relation between the measurement pixels (the dose measurement sensors, in general) and the grid is shifted, without using the huge number of calibration images.

SUMMARY OF THE INVENTION

An object of the present invention is to provide a radiation image detecting device that can precisely measure a radiation dose even if the positional relation between dose measurement sensors and a grid is shifted, and a radiation imaging system and an operation method thereof.

To achieve the above and other objects, a radiation image detecting device is used together with a grid, and an image detector disposed behind the grid has an imaging area is provided with a plurality of pixels and a plurality of dose measurement sensors. In at least a group of dose measurement sensors out of the plurality of dose measurement sensors, a [C/D] number of dose measurement sensors are disposed or chosen in the following cycle Z:

Condition:

$$Z=(R \times C) \pm D$$

wherein,

C represents a cycle of a repetition pattern appearing in a second direction in a radiographic image of the grid, and is represented in units of the number of the pixels, R represents a natural number of 0 or more, D represents an integer less than the cycle C, and

[C/D] represents a maximum integer equal to or less than C/D.

To remove scattered rays produced upon radiation passing through an object, the grid has strip-shaped radiation transparent layers and radiation absorbing layers, which extend in a first direction and are formed at a grid pitch G alternately in the second direction orthogonal to the first direction. The plurality of pixels, arrayed in the second direction at a pixel pitch Δ, accumulates electric charge in accordance with a received radiation dose in a readable manner to detect a radiographic image of the object. The plurality of dose measurement sensors measure the received radiation dose.

It is preferable that the radiation image detecting device further includes a judging section for judging an emission state of the radiation based on a measurement value of the group of dose measurement sensors, and a controller for performing control in accordance with a judgment result of the judging section.

The pixels preferably include a normal pixel for detecting the radiographic image, and a measurement pixel of the same size as the normal pixel and used as the dose measurement sensor. The normal pixel and the measurement pixel are preferably disposed in the first and second directions in two dimensions in a mixed manner.

The normal pixel and the measurement pixel are preferably connected to a common signal processing circuit. Electric charge of the normal pixel is accumulated and electric charge of the measurement pixel is read out to the signal processing circuit during emission of the radiation.

Provided that at least a [C/D] number of measurement pixels are shifted C occasions by one pixel, D preferably takes such a value that variations in output values of the

[C/D] number of measurement pixels on each occasion are within the range of ±k % (k<50).

The value of D is preferably determined by judging whether or not the variations in the output values on each occasion remain within the range of ±k % with reference to a minimum value of the output values on each occasion.

The group of the measurement pixels preferably allows the existence of an N number of measurement pixels satisfying the following conditional expression, in addition to the [C/D] number of measurement pixels:

Conditional Expression:

$$N \le \frac{[C/D]\{(1+k)Xave_{[C/D]min} - Xave_{[C/D]max}\}}{Xmin(a-k)}$$

wherein, $Xave_{[C/D]min}$ represents a minimum value of an average value of outputs of the [C/D] number of measurement pixels, $Xave_{[C/D]max}$ represents a maximum value of the average value of the outputs of the [C/D] number of measurement pixels, Xmin represents an output in a case where the N number of measurement pixels are disposed in the position of the pixels that are least susceptible to the radiation absorbing layers, and "a" represents a coefficient of variation representing the difference between a pixel value of the pixel that is the most susceptible to the radiation absorbing layer and a pixel value of the pixel that is the least susceptible to the radiation absorbing layer.

D=1 is preferable so that the output value on each occasion is invariable.

A tolerance in the variations is preferably k≤5 or k≤2.5.

In the case of selectively using a plurality of grids having different conditions of a disposition cycle Z of the group of the measurement pixels, a least common multiple of the plurality of disposition cycles Z is preferably used as a disposition cycle Z sharable among the plurality of grids.

In automatic exposure control, the judging section preferably judges whether or not a total radiation dose being an integrated value of a radiation dose measured by each of the measurement pixels or an average value of the total radiation doses has reached a target dose, and stops emission of the radiation in a case where the total radiation dose or the average value is judged to have reached the target dose.

It is preferable that the decision of the position of the group of measurement pixels stipulated in the second direction be also applied to the first direction.

The image detector is preferably an electronic cassette contained in a portable housing.

A radiation imaging system according to the present invention includes a radiation source for applying radiation to an object, a source control device for controlling the operation of the radiation source, and the radiation image detecting device described above.

An operation method of the radiation imaging system according to the present invention includes a radiation dose measuring step, a judging step, and a radiation emission stopping step. In the radiation dose measuring step, a radiation dose is measured by at least the group of dose measurement sensors out of the plurality of dose measurement sensors. In the judging step, it is judged whether or not a total radiation dose being an integrated value of each of the radiation doses measured by the group of the dose measurement sensors or an average value of the total radiation doses has reached a target dose. In the radiation emission stopping step, the operation of the radiation source is stopped to stop emission of the radiation, at the instant when the total radiation dose or the average value reaches the target dose.

According to the present invention, in the group of dose measurement sensors, the [C/D] number of dose measurement sensors are disposed or chosen in the cycle Z=(R×C) ±D. Therefore, it is possible to reduce variation in the output of the dose measurement sensors and precisely measure the radiation dose, even if the positional relation with the grid is shifted.

BRIEF DESCRIPTION OF THE DRAWINGS

For more complete understanding of the present invention, and the advantage thereof, reference is now made to the subsequent descriptions taken in conjunction with the accompanying drawings, in which:

FIG. 11 is a table showing output pattern variations in accordance with the number of the measurement pixels contained in one group based on which an AEC section calculates an average value of dose measurement signals, a sum value and the average value of the dose measurement signals;

FIG. 12 is a table showing the number of the measurement pixels contained in one group, a combination of a maximum value and a minimum value of the average values that can be brought by the listed number of measurement pixels, the maximum value/the minimum value, and a judgment on whether or not variations in the average values of the dose measurement signals by the listed number of measurement pixels are within a defined range;

DESCRIPTION OF THE PREFERRED EMBODIMENTS

Figure 1:
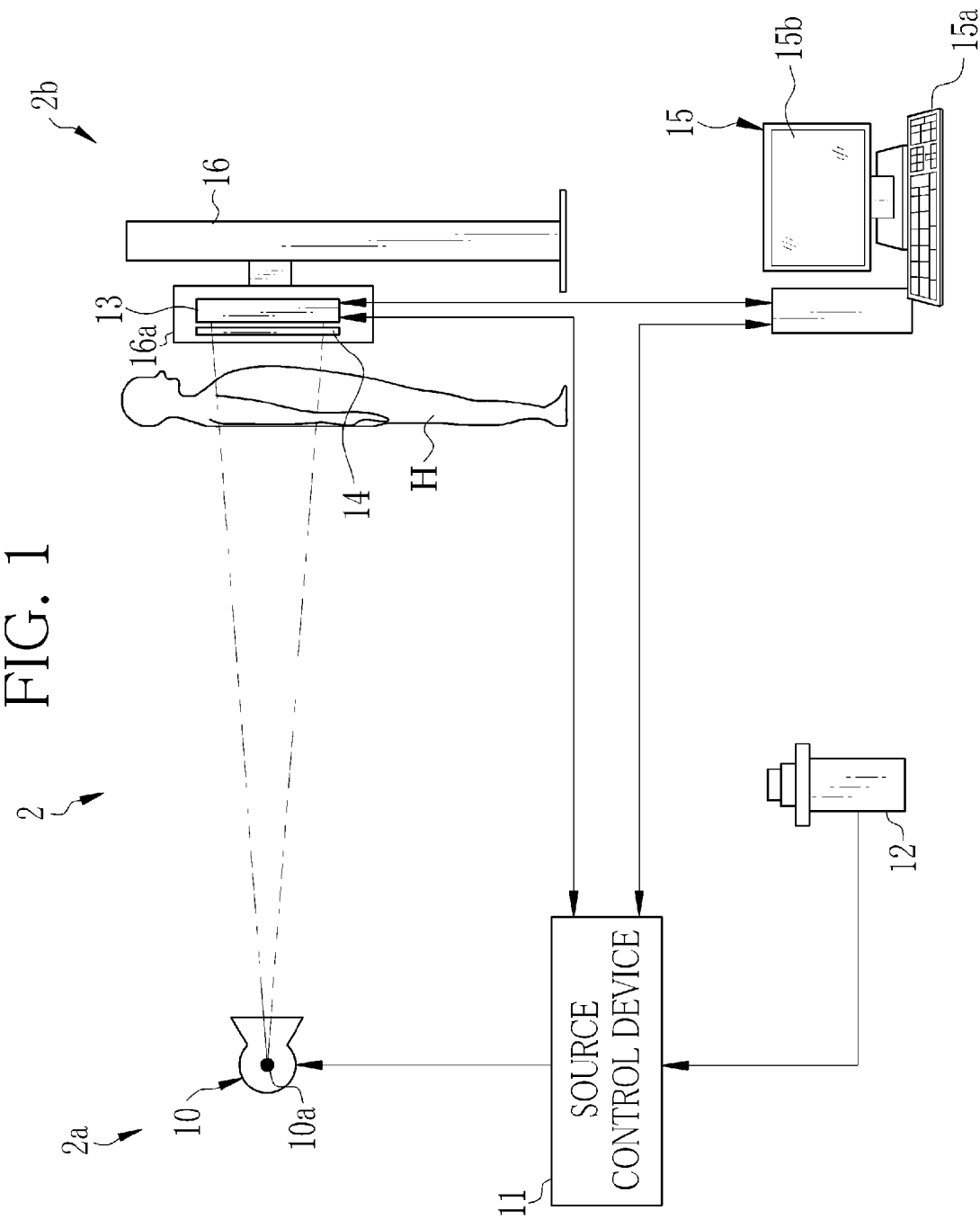
FIG. 1 is a schematic view of an X-ray imaging system.

As shown in FIG. 1, an X-ray imaging system 2 according to the present invention is constituted of an X-ray generating apparatus 2a and an X-ray imaging apparatus 2b. The X-ray generating apparatus 2a has an X-ray source 10, a source control device 11 for controlling the operation of the X-ray source 10, and an emission switch 12 for commanding the start of X-ray emission. The X-ray imaging apparatus 2b has an electronic cassette 13 for detecting X-rays passed through an object (a patient) H and outputting an X-ray image, a grid 14 for removing scattered radiation produced by the X-rays in passing through the object H, a console 15 for controlling the operation of the electronic cassette 13 and performing display processing of the X-ray image, and an imaging stand 16 for imaging the object H in a standing position. The electronic cassette 13 is used as a portable X-ray image detecting device. In addition to above, an imaging table for imaging the object H in a lying position, a source shift device for setting the X-ray source 10 in a desired orientation and position, and the like (none of them is shown in the drawing) are provided. The X-ray source 10 is used in a shared manner between the imaging stand and the imaging table.

The X-ray source 10 has an X-ray tube for radiating the X-rays and an irradiation field limiter (a collimator) for limiting an irradiation field of the X-rays. The X-ray tube has a cathode being a filament for emitting thermoelectrons, and an anode (a target) that radiates the X-rays by collision of the thermoelectrons emitted from the cathode. The X-rays radiates to every direction from a focal point 10a of the anode against which the thermoelectrons collide. The irradiation field limiter, for example, is composed of four lead plates for blocking the X-rays disposed on each side of a rectangle so as to form an irradiation opening in its middle through which the X-rays propagate. A shift of the lead plates varies the size of the irradiation opening to adjust the irradiation field.

The console 15 is wiredly or wirelessly connected to the electronic cassette 13 in a communicatable manner, and controls the operation of the electronic cassette 13 according to an input operation by an operator such as a radiological technician with an input device 15a such as a keyboard. The X-ray image is sent from the electronic cassette 13 to the console 15, and displayed on a display 15b. Also, the X-ray image is recorded to a storage device or a memory in the console 15, or data storage such as an image storage server connected to the console 15 through a network.

The console 15 displays an examination order, which includes information about the sex and the age of the object H, a body part to be imaged, a purpose of imaging, and the like, on the display 15b. The examination order is inputted from an external system, e.g. an HIS (hospital information system) or an RIS (radiography information system), that manages patient data and examination data related to radiography, or inputted manually by the operator from the input device 15a. The examination order includes the body part to be imaged e.g. head, chest, abdomen, or the like, and an imaging direction e.g. anterior, medial, diagonal, PA (the X-rays are applied from a posterior direction), AP (the X-rays are applied from an anterior direction), or the like. The operator confirms the contents of the examination order on the display 15b, and inputs an imaging condition corresponding to the contents of the examination order through an operation screen on the display 15b.

Figure 2:
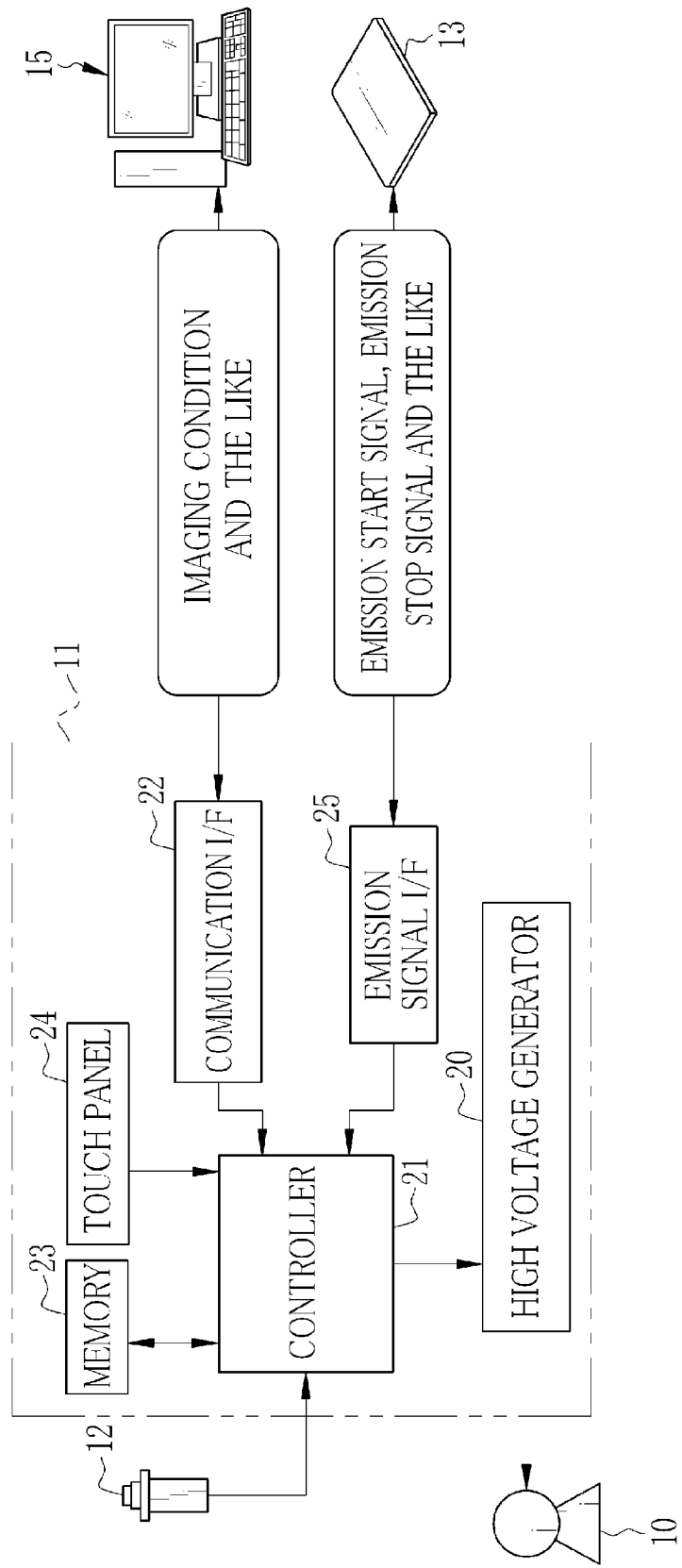
FIG. 2 is a block diagram of a source control device.

As shown in FIG. 2, the source control device 11 includes a high voltage generator 20, a controller 21, and a communication I/F 22. The high voltage generator 20 generates a high tube voltage by multiplying an input voltage by a transformer, and supplies the tube voltage to the X-ray source 10 through a high voltage cable. The controller 21 controls the tube voltage for determining an energy spectrum of the X-rays emitted from the X-ray source 10, a tube current for determining an emission amount per unit of time, and an emission time of the X-rays. The communication I/F 22 mediates transmission and reception of primary information and signals between the controller 21 and the console 15.

To the controller 21, the emission switch 12, a memory 23, and a touch panel 24 are connected. The emission switch 12 is, for example, a two-step push switch operated by the operator. Upon a first step push of the emission switch 12, a warm-up start signal is issued to start warming up the X-ray source 10. Upon a second step push, an emission start signal is issued to make the X-ray source 10 start the X-ray emission. These signals are inputted to the controller 21 through a signal cable. Upon receiving the emission start signal from the emission switch 12, the controller 21 starts supplying electric power for the X-ray emission from the high voltage generator 20 to the X-ray source 10.

The memory 23 stores several types of imaging conditions each including the tube voltage, the tube current, the emission time or a tube current-emission time product (mAs), and the like in accordance with the body part to be imaged and the like. The imaging condition is set manually by the operator through the touch panel 24. The source control device 11 controls the tube voltage and the tube current of the X-ray source 10 based on the set imaging condition, and controls a maximum driving time of the X-ray source 10. An automatic exposure control section (AEC section) 54 shown in FIG. 5 measures an X-ray dose (a time-integrated value), and stops the X-ray emission by the X-ray source 10 at the instant when the X-ray dose reaches a target dose determined in accordance with the imaged body part and the like, even if the emission time or the tube current-emission time product according to the imaging condition has not elapsed. The emission time or the tube current-emission time product is set at a larger value with an allowance in the case of using the AEC section 54 than in the case of not using the AEC section 54, for the purpose of preventing a situation in which the X-ray emission is completed based on the imaging condition before the AEC section 54 stops the X-ray emission and thereby the X-ray dose becomes insufficient. For example, as the emission time in the case of using the AEC section 54, a maximum emission time that is allowable under safety regulations in accordance with the body part to be imaged may be used.

An emission signal I/F 25 is wiredly or wirelessly connected to the electronic cassette 13 in the case of using the AEC section 54. In this case, upon receiving the warm-up start signal from the emission switch 12, the controller 21 transmits an emission start request signal, which queries whether or not the X-ray emission can be started, to the electronic cassette 13 thorough the emission signal I/F 25. Upon receiving the emission start request signal, the electronic cassette 13 checks whether or not the electronic cassette 13 is ready for imaging, and transmits an emission permission signal if the electronic cassette 13 is ready for imaging. Upon receiving the emission permission signal through the emission signal I/F 25 and receiving the emission start signal from the emission switch 12, the controller 21 makes the high voltage generator 20 supply the X-ray source 10 with electric power of the high voltage to start the X-ray emission. Moreover, the controller 21 stops the electric power supply from the high voltage generator 20 to the X-ray source 10 to stop the X-ray emission, upon receiving an emission stop signal from the electronic cassette 13 through the emission signal I/F 25.

Figure 3:
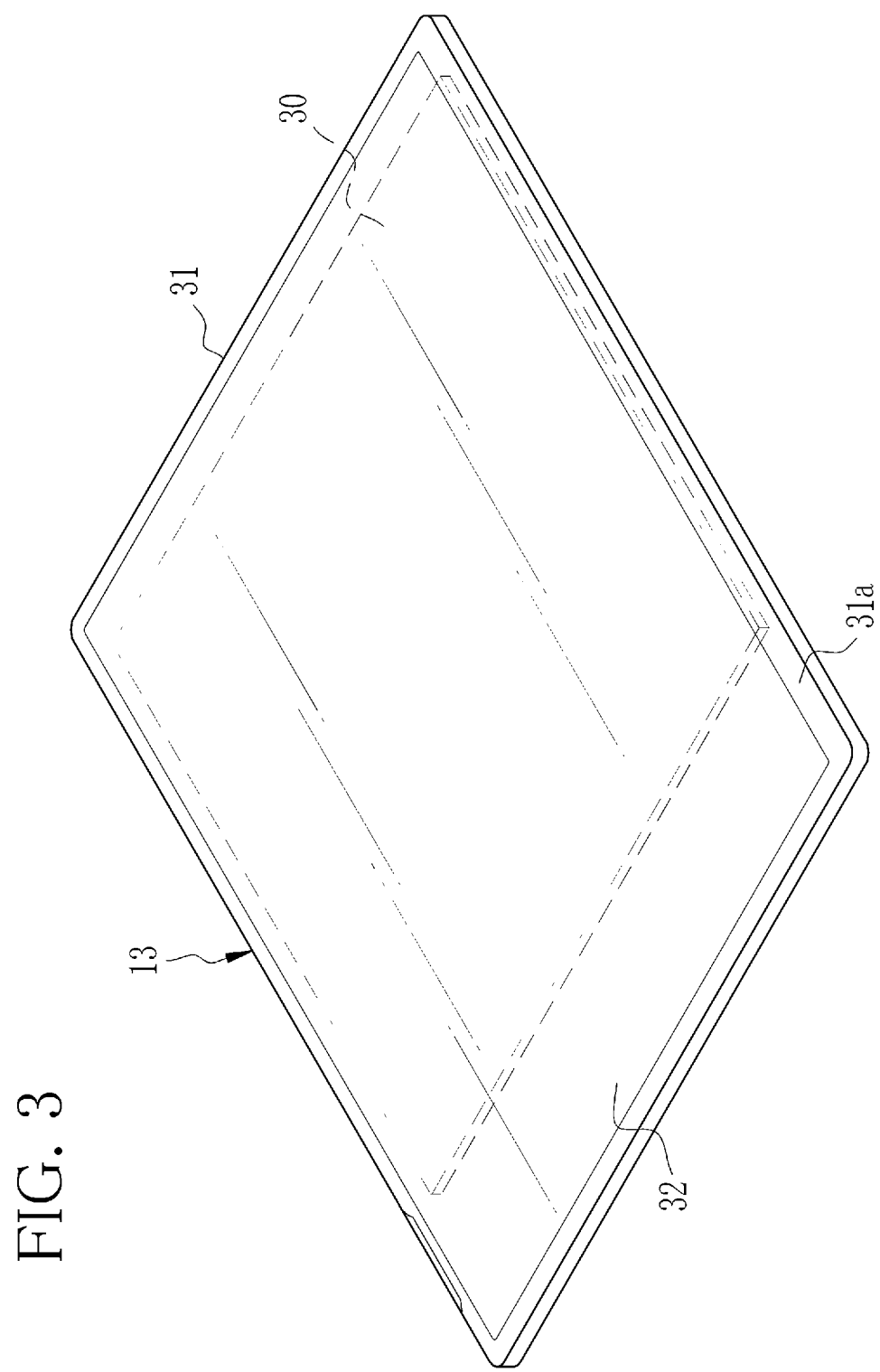
FIG. 3 is a perspective view of an electronic cassette.

In FIG. 3, the electronic cassette 13 is constituted of an image detector 30 and a portable flat box-shaped housing 31 containing the image detector 30. As the image detector 30, a well-known flat panel detector (FPD) is used. The housing 31 is made of a conductive resin, for example, and formed with a rectangular opening at its front panel 31a upon which the X-rays are incident. A top plate 32 made of an X-ray transparent material is attached to the housing 31 so as to be fitted into the opening. The top plate 32 is made of a material of light weight, high stiffness, and high X-ray transmittance, e.g. a carbon material. The housing 31 has the function of an electromagnetic shield, which prevents entry of electromagnetic noise to the electronic cassette 13 and radiation of electromagnetic noise from the electronic cassette 13 to the outside. Note that, the housing 31 contains a battery (a secondary battery) for supplying electric power to drive the electronic cassette 13, an antenna for establishing wireless communication of data including the X-ray image and the like with the console 15, and the like.

The housing 31 adheres to the International Standard ISO 4090:2001 related to a film cassette, an IP cassette, and a CR cassette, and is of the same size as the film cassette, the IP cassette, and the CR cassette. The electronic cassette 13 is detachably set in a holder 16a (see FIG. 1) of the imaging stand 16 or a holder of the imaging table, and held in such a position that an imaging area 41 (see FIG. 5) is opposed to the X-ray source 10. The X-ray source 10 is shifted by the source shift device attached to a ceiling of an imaging room or the like, according to the imaging stand or the imaging table to be used. The electronic cassette 13 is sometimes used by itself in a state of being put on a bed under the object H lying or held by the object H himself/herself, instead of being set in the imaging stand 16 or the imaging table. Also, the electronic cassette 13 is compatible with the film cassette, the IP cassette, and the CR cassette, and can be mounted on an existing imaging stand or imaging table designed for the film cassette, the IP cassette, and the CR cassette.

Figure 4:
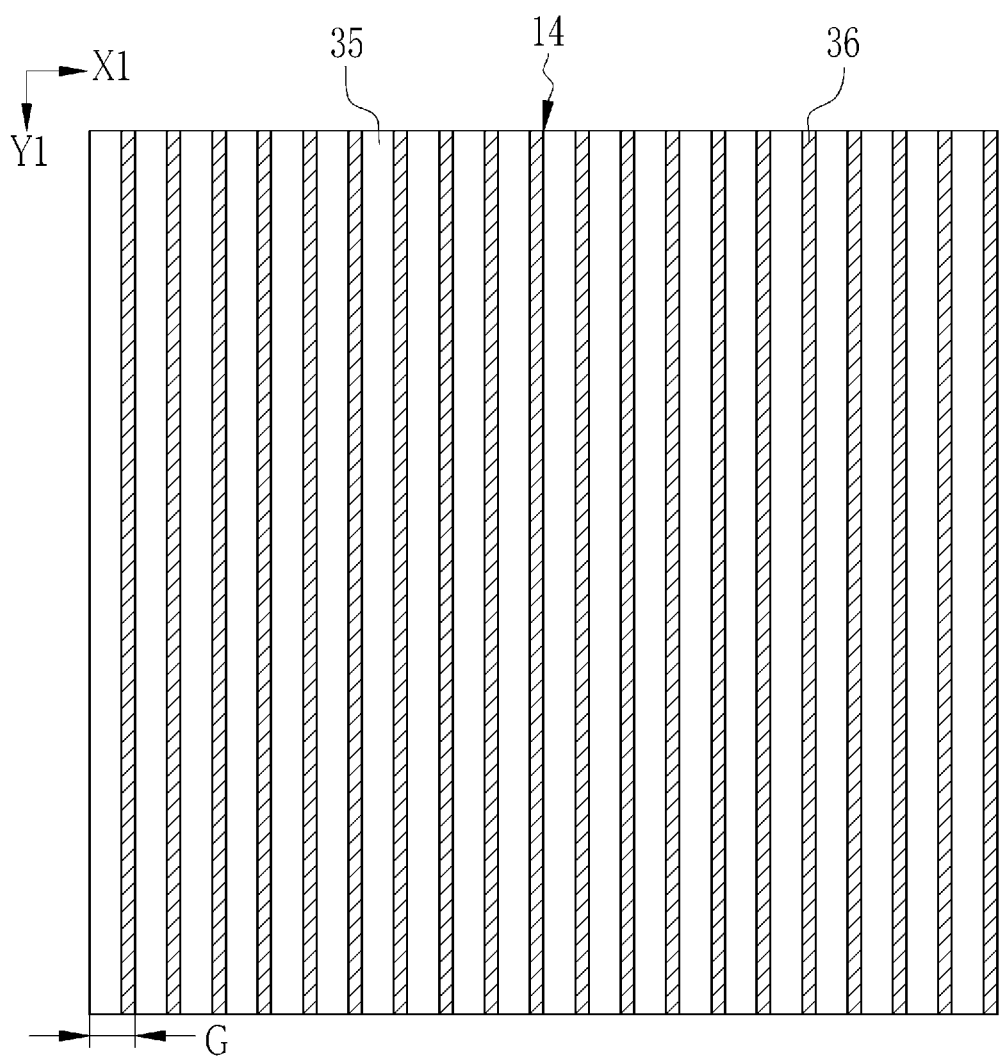
FIG. 4 is a plan view of a grid.

In FIG. 4, the grid 14 is made of a thin plate of approximately the same size as the housing 31. The grid 14 is detachably loaded to the holder 16a so as to be disposed in front of the electronic cassette 13 (see FIG. 1). The grid 14 can be exchanged for another grid in accordance with the purpose of imaging, or detached from the holder 16a in imaging without using the grid. The holder 16a has no mechanism for swinging the grid 14, and therefore the grid 14 is a so-called static grid, which does not swing.

In this embodiment, the grid 14 is directly inserted into the holder 16a. However, the grid 14 may be contained in an X-ray transparent housing to protect the grid 14, and the housing may be loaded into the holder 16a. Otherwise, the grid 14 may be provided within the housing 31 in manufacturing the electronic cassette 13, instead of providing the grid 14 separate from the electronic cassette 13. Otherwise, a grid holder may be provided on the front panel 31a of the housing 31 of the electronic cassette 13, and the grid 14 may be detachably attached to the grid holder. Also in this case, the grid 14 can be exchanged or detached in X-ray imaging in accordance with the purpose of imaging.

The grid 14 has strip-shaped X-ray transparent layers 35 and X-ray absorbing layers 36 (shown with hatching) extending in a Y1 direction (a first direction). A plurality of the layers 35 and 36 are arranged alternately in an X1 direction (a second direction) orthogonal to the Y1 direction at a predetermined grid pitch (an arrangement pitch of the X-ray absorbing layers 36) G. The X-ray transparent layer 35 is made of an X-ray transparent material such as aluminum, or a gap. The X-ray absorbing layer 36 is made of a material that absorbs the X-rays and blocks the X-rays from transmitting, such as lead, a molybdenum alloy, or a tantalum alloy. The grid 14 is set in the holder 16a such that the arrangement direction X1 of each layer 35, 36 coincides with a row direction X2 (see FIG. 5) of pixels 40 of the image detector 30.

The number of the X-ray absorbing layers 36 in the arrangement direction X1 per unit length is 32/cm to 100/cm, for example. Thus, the grid pitch G is 100 µm to approximately 300 µm.

Figure 5:
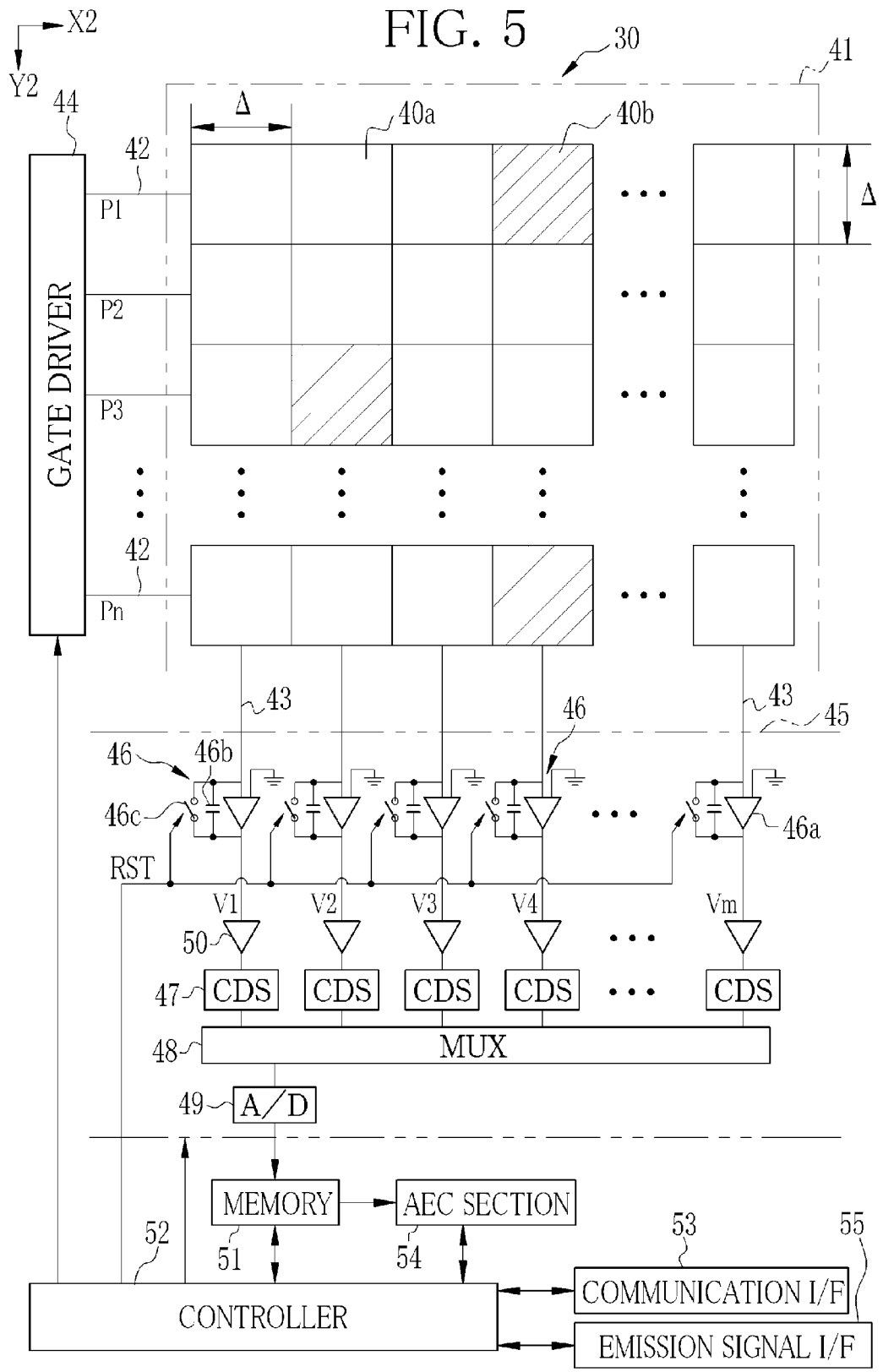
FIG. 5 is a block diagram showing the structure of the electronic cassette.

In FIG. 5, the image detector 30 has a TFT active matrix substrate (not shown), and the imaging area 41 is formed on this substrate. The imaging area 41 is provided with a plurality of pixels 40, which produce electric charge in accordance a received X-ray dose, arrayed into a matrix of n rows (along the X2 direction)×m columns (along the Y2 direction) at a predetermined pitch Δ (for example, 100 µm to 200 µm).

The image detector 30 is, for example, of an indirect conversion type having a scintillator (not shown) made of a phosphor. In the image detector 30, the pixels 40 perform photoelectric conversion of visible light converted by the scintillator. As is widely known, the scintillator is made of CsI:Tl (thallium activated cesium iodide), GOS ($Gd_2O_2S$:Tb terbium activated gadolinium oxysulfide), or the like, and is opposed to the entire imaging area 41 having an array of the pixels 40. Note that, the scintillator and the TFT active matrix substrate may adopt either a PSS (penetration side sampling) method in which the scintillator and the substrate are disposed in this order from an X-ray incident side, or an ISS (irradiation side sampling) method in which the substrate and the scintillator are disposed in this order. Instead of above, the image detector 30 may be of a direct conversion type, which uses a conversion layer (amorphous selenium or the like) for directly converting the X-rays into the electric charge without using the scintillator.

As is widely known, the pixel 40 is provided with a photoelectric converter for producing the electric charge (electron and positive hole pairs) upon entry of the visible light, and the TFT being a switching element (none of them is illustrated). Note that, since space between the pixels 40 is omitted in FIG. 5, a pixel pitch Δ represents the width of the pixels 40. However, the pixel pitch Δ is the distance between the centers of the photoelectric converters of the two pixels 40 adjoining each other.

The pixels 40 include normal pixels 40*a* and measurement pixels 40*b*. The normal pixels 40*a* are used to detect the X-ray image, and the electric charge accumulated in the normal pixels 40*a* is read out after completion of X-ray imaging. The measurement pixels 40*b* are used to measure the X-ray dose, and the electric charge is taken out of the measurement pixels 40*b* during the X-ray imaging. The measurement pixels 40*b* function as dose measurement sensors, which measure the X-ray dose received by the imaging area 41, and are used for AEC, for example. Note that, the measurement pixels 40*b* are hatched for the purpose of distinction from the normal pixels 40*a*.

First, the structure of the normal pixel 40*a* will be described. As is widely known, the photoelectric converter has a semiconducting layer (of a PIN (p-intrinsic-n) type, for example) for producing the electric charge, and upper and lower electrodes disposed on the top and bottom of the semiconducting layer. The lower electrode is connected to the TFT, and the upper electrode is connected to a bias line. The number of the bias lines coincides with the number of rows (n rows) of the normal pixels 40*a*. These bias lines are connected to a bias power source through one bus. Since application of a bias voltage by the bias power source produces an electric field in the semiconducting layer, the electric charge (electron and positive hole pairs) produced in the semiconducting layer by the photoelectric conversion is attracted to the upper and lower electrodes, one of which has positive polarity and the other has negative polarity, and thereby the electric charge is accumulated in the photoelectric converter.

A gate electrode of the TFT is connected to a scan line 42. A source electrode of the TFT is connected to a signal line 43. A drain electrode of the TFT is connected to the photoelectric converter. The scan lines 42 are wired in a row direction, and the signal lines 43 are wired in a column direction. Since one scan line 42 is assigned to the pixels 40 of one row, the number of the scan lines 42 coincides with the number of the rows (n rows) of the pixels 40. Likewise, since one signal line 43 is assigned to the pixels 40 of one column, the number of the signal lines 43 coincides with the number of the columns (m columns) of the pixels 40. Each scan line 42 is connected to a gate driver 44, and each signal line 43 is connected to a signal processing circuit 45.

The gate driver 44 performs an accumulation operation for accumulating the signal charge in the normal pixels 40*a* in accordance with the received X-ray dose, a readout (actual reading) operation for reading out the accumulated signal charge from the normal pixels 40*a*, and a reset (idle reading) operation, by driving the TFTs under control by a controller 52. In the accumulation operation, the TFTs are in an off state, and the signal charge produced during that time is accumulated in the normal pixels 40*a*. The readout operation is carried out immediately after X-ray imaging. In this readout operation, the gate driver 44 sequentially issues gate pulses P1 to Pn at predetermined intervals to activate the scan lines 42 one by one in a sequential manner. Thus, the TFTs of one row connected to the activated scan line 42 are turned into an on state. Upon turning on the TFTs, the electric charge accumulated in the normal pixels 40*a* is read out to the signal lines 43 and sent to the signal processing circuit 45.

The measurement pixel 40*b* is used for measuring the X-ray dose, and has the same fundamental structure including the photoelectric converter and the like as the normal pixel 40*a*. However, in the measurement pixel 40*b*, the source electrode and the drain electrode of the TFT are shorted out. Thus, the electric charge produced by the photoelectric converter of the measurement pixel 40*b* flows into the signal line 43, irrespective of the turn-on and -off of the TFT. Therefore, it is possible to take out the signal charge from the measurement pixel 40*b*, even if the normal pixels 40*a* in the same row have the TFTs being turned off and are in the accumulation operation of the signal charge.

The signal processing circuit 45 includes integrating amplifiers 46, amplifiers 50, and CDS circuits (CDSs) 47 provided to signal lines 43 on a one-to-one basis, and a multiplexer (MUX) 48 and an A/D converter (A/D) 49 used in a shared manner among the signal lines 43. The integrating amplifier 46 is composed of an operational amplifier 46*a* and a capacitor 46*b* connected between input and output terminals of the operational amplifier 46*a*, and the signal line 43 is connected to one of the input terminals of the operational amplifier 46*a*. The other input terminal of the operational amplifier 46*a* is connected to a ground (GND). A reset switch 46*c* is connected in parallel with the capacitor 46*b*. The CDS 47, having a sample hold circuit, applies correlated double sampling to an output voltage signal of the integrating amplifier 46 to remove noise, and holds (sample-holds) the voltage signal of the integrating amplifier 46 for a predetermined time period at the sample hold circuit. The MUX 48 chooses one of the CDSs 47, which are provided on a column-by-column basis and connected in parallel, in turn with the use of an electronic switch based on an operation control signal from a shift register (not shown). The voltage signals of the chosen CDSs 47 are inputted in series to the A/D 49. The A/D 49 converts the voltage signals into digital voltage signals, and outputs the digital voltage signals to a memory 51 as image data of one row. Note that, another amplifier may be connected between the MUX 48 and the A/D 49.

In the readout operation of the normal pixels 40*a*, the integrating amplifiers 46 integrate the signal charge that is taken out of the normal pixels 40*a* of the activated row through the signal lines 43, and convert the signal charge into analog voltage signals V1 to Vm. Each of the voltage signals V1 to Vm of the integrating amplifiers 46 is amplified by the amplifier 50 and sent to the CDS 47. After the noise removal by the CDS 47, the voltage signals V1 to Vm are taken out in turn by the MUX 48 and converted into the digital data by the A/D 49. The memory 51 records the image data associated with the coordinates of the normal pixels 40*a* on a row-by-row basis.

During X-ray imaging, the signal charge produced in the measurement pixels 40*b* flows into the integrating amplifiers 46 through the signal lines 43. Provided that there are a plurality of measurement pixels 40*b* in the same column, the capacitor 46*b* integrates the electric charge of the measurement pixels 40*b*. The integrating amplifiers 46 are reset at regular time intervals, and thus a plurality of number of measurements are carried out. Output voltages of the integrating amplifiers 46 are taken out whenever the measurement is performed, and converted into the digital voltage signals (hereinafter called dose measurement signals) by the A/D 49. The dose measurement signals are sent to the memory 51 as measurement values. The memory 51 records the measurement values in associated with the coordinate information of each measurement pixel 40*b* in the imaging area 41, and update the measurement values at regular time intervals.

In the pixels 40 (both of the normal pixels 40*a* and the measurement pixels 40*b*), dark charge occurs in the semiconducting layer of the photoelectric converter irrespective of the presence or absence of entry of the X-rays. Due to the application of the bias voltage, the dark charge is accumulated in the photoelectric converter of each pixel 40. The dark charge occurring in the pixels 40 becomes a noise component of the image data, and therefore the reset operation is performed at the regular time intervals to remove the noise component. The reset operation is an operation in which the dark charge produced in the pixels 40 is discharged through the signal lines 43.

The reset operation adopts a sequential reset method, for example, by which the pixels 40 are reset on a row-by-row basis. In the sequential reset method, just as with the readout operation of the signal charge, the gate driver 44 sequentially issues gate pulses P1 to Pn at predetermined intervals to the scan lines 42 to turn on the TFTs of the pixels 40 on a row-by-row basis. While the TFT is turned on, the dark charge flows from the pixel 40 through the signal line 43 into the capacitor 46*b* of the integrating amplifier 46. In the reset operation, in contrast to the readout operation, the MUX 48 does not read out the electric charge accumulated in the capacitors 46*b*. In synchronization with the issue of each of the gate pulses P1 to Pn, the controller 52 outputs a reset pulse RST to turn on the reset switches 46*c*. Thereby, the electric charge accumulated in the capacitors 46*b* is discharged, and the integrating amplifiers 46 are reset.

Instead of the sequential reset method, a parallel reset method in which a plurality of rows of the array of the pixels are grouped together and the sequential reset is carried out in each group so as to concurrently discharge the dark charge from the rows of the number of the groups, or all pixels reset method in which the gate pulse is inputted to every row to discharge the dark charge from every pixel at a time may be used. The parallel reset method and the all pixels reset method allow speeding up the reset operation.

The controller 52 is provided with various image processing circuits (not shown) that apply an offset correction, a sensitivity correction, and a defect correction to the X-ray image data of the memory 51. The offset correction circuit subtracts an offset correction image, which is captured by the image detector 30 without applying the X-rays, from the X-ray image to remove fixed pattern noise caused by the individual difference of the signal processing circuit 45 or an imaging environment. The sensitivity correction circuit, which is also called gain correction circuit, corrects sensitivity variations in the photoelectric converters of the pixels 40, variations in the output properties of the signal processing circuit 45, and the like. The defect correction circuit performs linear interpolation of a pixel value of a defect pixel with a pixel value of a normal pixel in the vicinity thereof, based on defect pixel information produced in shipping or a routine check. In the defect correction circuit, the measurement pixel 40*b* is treated as a defect pixel. Since an output of the measurement pixel 40*b* that constantly flows out affects pixel values of the normal pixels 40*a* in the same column as the measurement pixel 40*b*, the defect correction circuit applies the defect correction by the linear interpolation to the pixel values of the normal pixels 40*a* in the same column as the measurement pixel 40*b* too. Note that, the above-described various image processing circuits may be provided in the console 15, and the console 15 may perform the various types of image processing.

Whenever one measurement is carried out, the controller 52 reads out the dose measurement signals (the measurement values) obtained in this measurement and integrated measurement values (integrated X-ray doses) until the last measurements from the memory 51, and calculates new integrated measurement values by integration on a measurement pixel 40*b* basis, and overwrites the new integrated measurement values to the memory 51. The AEC section 54 takes out the integrated measurement values of all or part of the measurement pixels 40*b* included in a measurement area, and obtains an average value (an average integrated X-ray dose) by an arithmetic average. At the instant when the obtained average value reaches an emission stop threshold value (a target dose), the emission stop signal is produced. This emission stop signal is outputted from an emission signal I/F 55 through the controller 52. To the emission signal I/F 55, the emission signal I/F 25 of the source control device 11 is connected wiredly or wirelessly. The emission signal I/F 55 performs reception of the emission start request signal, transmission of the emission permission signal in response to the emission start request signal, reception of the emission start signal, and transmission of the emission stop signal outputted from the AEC section 54.

Next, the operation of the X-ray imaging system 2 will be described. Before performing X-ray imaging, preparations for the imaging are performed. First, the electronic cassette 13 is loaded into the imaging stand or the imaging table, e.g. the holder 16*a* of the imaging stand 16. In imaging using a grid, the grid 14 is loaded into the holder 16*a* to dispose the grid 14 in front of the electronic cassette 13. With referring to the examination order displayed on the display 15*b*, the imaging condition including the tube voltage, the tube current, the emission time, the body part to be imaged, and the like is inputted with operation of the touch panel 24 or the like. Then, the object H is made stand in front of the imaging stand 16, and the measurement area is set in accordance with the body part to be imaged. For example, in a case where the body part to be imaged of the object H is the chest, areas corresponding to left and right lung fields in the imaging area 41 are designated as the measurement areas. Completion of the preparations for imaging enables the X-ray imaging.

The electronic cassette 13 loaded into the holder 16*a* is set in a standby mode. In the standby mode, the dark charge is produced in each pixel 40 of the image detector 30, even though the X-rays are not applied thereto. To remove the dark charge being the noise component, the reset operation is applied at predetermined time intervals to the image detector 30 during the preparations for the X-ray imaging (before the X-ray imaging). In the reset operation, the gate driver 44 sequentially issues the gate pulses P1 to Pn to the scan lines 42 so as to turn on the TFTs of the normal pixels 40*a* on a row-by-row basis. Upon turning on the TFTs of the normal pixels 40*a* of one row, the dark charge accumulated in these normal pixels 40*a* is readout and sent to the integrating amplifiers 46. In the reset operation, the MUX 48 does not take out the voltage converted by the integrating amplifiers 46.

In the reset operation, the controller 52 outputs the reset pulse RST with a predetermined time difference from each of the gate pulses P1 to Pn. Since the reset pulse RST turns on the reset switches 46*c*, the dark charge accumulated in each capacitor 46*b* is discharged so as to reset the integrating amplifiers 46. As for the measurement pixels 40*b*, the dark charge flows into the integrating amplifiers 46 irrespective of each of the gate pulses P1 to Pn, because the TFTs are shorted out. Thus, the dark charge from the measurement pixels 40*b* is discarded together with the dark charge of the normal pixels 40*a*. Note that, the reset switches 46*c* may be kept in an on state during the reset operation.

After the preparations for X-ray imaging, the X-ray source 10 is warmed up by a first step push of the emission switch 12. Then, the emission start signal is issued by a full push of the emission switch 12. This emission start signal is inputted to the controller 21 of the source control device 11, so that the X-ray imaging is started. The emission start signal is also inputted to the electronic cassette 13 through the emission signal I/F 25. The electronic cassette 13 is changed from the standby mode to an imaging mode, and the image detector 30 is shifted from the reset operation to the accumulation operation. Concurrently with this, automatic exposure control is started based on a dose measurement with the use of the measurement pixels 40b.

Upon starting the X-ray imaging, the X-ray source 10 is actuated by the high voltage from the high voltage generator 20. The X-ray source 10 emits and applies the X-rays to the body part to be imaged of the object H. The X-rays passed through the body part are incident upon the grid 14. The grid 14 blocks the X-rays at the X-ray absorbing layers 36, while passes the X-rays at the X-ray transparent layers 35. The X-rays passed through the X-ray transparent layers 35 are incident upon the electronic cassette 13. The X-rays that are incident upon the electronic cassette 13 are converted into the visible light at the image detector 30. This visible light is converted into the electric charge at the photoelectric converter of each pixel 40. During the accumulation operation of the image detector 30, the TFTs are in an off state, and thus each of the normal pixels 40a accumulates the produced electric charge in the photoelectric converter.

Since the TFTs of the measurement pixels 40b are shorted out, the electric charge produced in the photoelectric converters of the measurement pixels 40b flows into the signal lines 43, irrespective of the turn-on and -off of the TFTs, during the accumulation operation of the image detector 30. Thus, the electric charge of each measurement pixel 40b is accumulated in the capacitor 46b of the corresponding integrating amplifier 46. The reset switch 46c of each integrating amplifier 46 is usually turned off, but turned on once every regular time period to reset the integrating amplifiers 46. The time duration of the turn-off of the reset switches 46c after the turn-on is designated as one measurement period, and the X-ray dose per predetermined time is measured. The X-ray dose is measured in relatively short cycles, and integrating a measurement value of each time allows measurement of the X-ray dose on a measurement pixel 40b basis. Note that, the reset switch 46c of the integrating amplifier 46 may be kept in an off state and a voltage of each integrating amplifier 46 may be read out in relatively short cycles. This allows taking out an integrated measurement value in each cycle, and hence eliminates the need for integrating the measurement value of each time.

In a first measurement, an output voltage of the integrating amplifier 46 is multiplied by the amplifier 50 and sent to the CDS 47. This CDS 47 samples the output voltages of the integrating amplifier 46 at the start and the end of the one measurement, and calculates the difference therebetween to remove noise. The output voltages of CDSs 47 are sequentially taken out by the MUX 48 and sent to the A/D 49. The A/D 49 converts the output voltages into digital data, and the digital data is sent to the memory 51 as the dose measurement signals per predetermined time. The memory 51 records the dose measurement signals each of which is associated with the coordinate information of the measurement pixel 40b in a first memory area as first measurement values.

The AEC section 54 chooses the measurement pixels 40b of a minimum unit (called a group of measurement pixels 40b) that are included in the designated measurement area and the effect of a positional shift of the grid 14 can be compensated even if the positional shift of the grid 14 occurs. This group of measurement pixels 40b may contain one measurement pixel 40b or a plurality of measurement pixels 40b situated in different positions in the measurement area. Furthermore, all the measurement pixels 40b included in the designated measurement area may be designated as the chosen measurement pixels for use in the automatic exposure control.

The AEC section 54 calculates an average value of the measurement values of the chosen measurement pixels. Then, the AEC section 54 compares the calculated average value with the predetermined emission stop threshold value. In a case where the average value does not reach the emission stop threshold value, a second X-ray measurement is performed in synchronization with the operation of the reset switches 46c. Note that, instead of the average value, a sum value of the measurement values may be calculated and the sum value may be compared with another emission stop threshold value that is set in accordance with the sum value.

In the second X-ray measurement, just as with the first X-ray measurement, the output voltages of the integrating amplifiers 46 are taken out and sent to the memory 51 as second measurement values. The second measurement values associated with the coordinate information of the measurement pixels 40b are recorded to a second memory area. After the recording, the controller 52 adds the second measurement value to the first measurement value recorded in the first memory area on a measurement pixel-by-measurement pixel basis, and updates the measurement value of the first memory area with the obtained integrated measurement value (integrated X-ray dose). After the update, the AEC section 54 reads out the integrated measurement value of each chosen measurement pixel from the first memory area, and calculates an average value thereof. The AEC section 54 compares the calculated average value with the emission stop threshold value. In a case where the average value according to the second measurement does not reach the emission stop threshold value, a third X-ray measurement is performed in the procedure described above.

In a case where the average value of the integrated measurement values has reached the emission stop threshold value while the X-ray measurements are repeated, the AEC section 54 judges that appropriate exposure is carried out. In this case, the controller 52 sends the emission stop signal to the source control device 11 through the emission signal I/F 55. Upon receiving the emission stop signal from the electronic cassette 13, the source control device 11 stops the operation of the high voltage generator 20. Thus, the X-ray source 10 stops the X-ray emission and completes the X-ray imaging.

After the electronic cassette 13 commands the source control device 11 to end the X-ray imaging, the image detector 30 starts the readout operation. At the start of the readout operation, every reset switch 46c is turned on and every integrating amplifier 46 is reset. Thus, the electric charge from the measurement pixels 40b is discarded. Then, after every reset switch 46c is turned off, the gate driver 44 issues the gate pulse P1 for the first row. This gate pulse P1 activates the scan line 42 of the first row, and turns on the TFTs connected thereto. Upon turning on the TFTs, the electric charge accumulated in the normal pixels 40a of the first row flows into the integrating amplifiers 46 through the signal lines 43. The integrating amplifiers 46 convert the signal charge of each normal pixel 40a into voltages. The voltages are recorded to the memory 51 as the X-ray image data of the first row through the amplifiers 50, the CDSs 47, the MUX 48, and the A/D 49.

After the image data of the first row is written to the memory 51, the controller 52 outputs the reset pulse RST to the integrating amplifiers 46 to turn on and off the reset switches 46c. Thus, the signal charge accumulated in each capacitor 46c is discharged. After the reset of the integrating amplifiers 46, the gate driver 44 outputs the gate pulse P2 of the second row to start reading out the signal charge from the normal pixels 40a of the second row. The X-ray image data of the second row obtained in this manner is written to the memory 51.

In a like manner, the gate driver 44 sequentially issues the gate pulses P3 to Pn of third to n-th rows to read out the electric charge from the normal pixels 40a of the third to n-th rows. The electric charge is converted into the X-ray image data of the third to n-th rows, and written to the memory 51.

The controller 52 applies various types of image processing including the offset correction, the sensitivity correction, and the defect correction to the X-ray image written to the memory 51. The offset correction eliminates fixed pattern noise caused by the individual difference of the signal processing circuit 45 or an imaging environment. The sensitivity correction corrects sensitivity variations among the photoelectric converters of the normal pixels 40a, variations in the output properties of the signal processing circuit 45, and the like. The defect correction performs linear interpolation of defect pixels identified beforehand, the measurement pixels 40b, and the normal pixels 40a arranged in the same column as the measurement pixel 40b, with the use of the pixel values in the vicinity thereof.

The X-ray image in the memory 51, after being subjected to the image processing, is sent from the electronic cassette 13 through a communication I/F 53 to the console 15. In this console 15, the X-ray image is displayed on the display 15b and used in a medical diagnosis. The X-ray image sent to the console 15 is saved to the storage device in the console 15 or the image storage server connected to the console through the network.

Imaging without using the grid is the same as imaging with using the grid, except that the grid 14 is removed from the imaging stand or the imaging table. The dose measurement signals obtained in the imaging without using the grid are larger than those obtained in the imaging with using the grid, because none of the measurement pixels 40b is subjected to X-ray absorption by the grid 14. Accordingly, the emission stop threshold value (the target value) is set higher in the imaging without using the grid than in the imaging with using the grid, in order to equalize an X-ray irradiation amount (an exposure amount) of the object H between the imaging with using the grid and the imaging without using the grid.

In the above embodiment, the emission stop signal is issued at the instant when the average value of the integrated measurement values of the measurement pixels 40b reaches the emission stop threshold value. Instead of this, predicted time of reaching the target dose (an X-ray dose per unit of time) may be calculated from X-ray intensity, and the emission stop signal may be sent to the source control device 11 when the calculated predicted time has elapsed. Note that, information on the predicted time itself may be sent to the source control device 11, and the X-ray source 10 may stop the X-ray emission when the source control device 11 detects the elapse of the predicted time.

The type and the like of the grid 14 have an effect on the measurement of the X-ray dose. Therefore, by performing pre-imaging in which a low dose of X-rays is applied to the object, the emission time or the tube current-emission time product for actual X-ray imaging may be determined based on the measurement of the X-ray dose in the pre-imaging.

The electronic cassette 13 and the grid 14 are sometimes set in the imaging stand or the imaging table in a state of being shifted from a designed positional relation. Otherwise, while the electronic cassette 13 and the grid 14 are loaded into the imaging stand or the imaging table, the positional relation between the electronic cassette 13 and the grid 14 is sometimes changed by vibration or the like. The present invention reduces variation in the measurement value of the measurement pixel so as to eliminate the effect of the shift in the positional relation between the electronic cassette 13 and the grid 14 on the dose measurement by devising the disposition of the measurement pixels. Disposition examples of the measurement pixels that allow reducing the variation of the measurement value will be hereinafter described.

Figure 6:
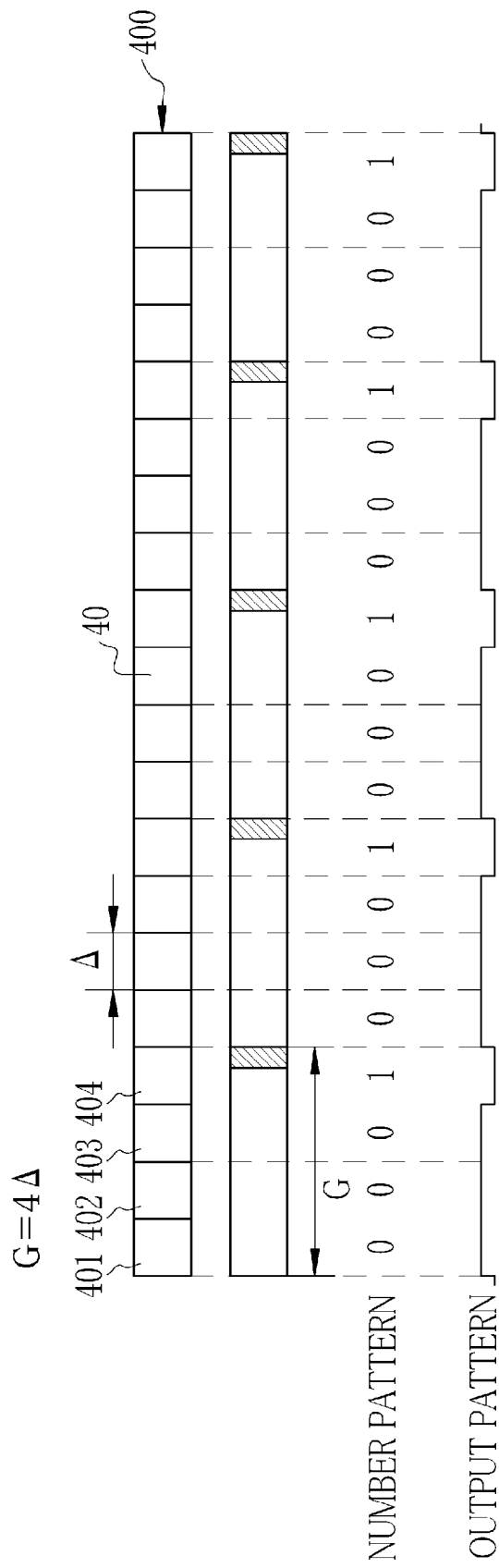
FIG. 6 is an explanatory view of an output waveform from each pixel in a case where a grid pitch G is four times as large as a pixel pitch Δ.

As a first step, an explanation is given with taking FIG. 6 as an example. A pixel array 400 shown in FIG. 6 is a part of one row of the pixels 40 that are taken out of the image detector 30 shown in FIG. 5. FIG. 6 shows the positional relation between the pixels 40 and the X-ray absorbing layers 36, a pattern of the number (hereinafter called number pattern) of the X-ray absorbing layers 36 projected to the pixels 40 in capturing a stripe-patterned image of the grid 14 corresponding to each of the layers 35 and 36 without disposing the object H, and a pattern of an output level (hereinafter called output pattern) of the voltage signal measured by each pixel 40, which varies depending on the positional relation and the number pattern, in a case where the grid pitch G is four times as large as the pixel pitch $\Delta$ ($G=4\Delta$).

As for the number of the X-ray absorbing layers 36 projected to the pixel 40, for example, leftmost three pixels 401 to 403 are opposed to no X-ray absorbing layer 36, so the number of the X-ray absorbing layers 36 projected thereto is zero. On the other hand, a fourth pixel 404 next to the pixel 403 on the right is opposed to one X-ray absorbing layer 36, so the number of the X-ray absorbing layers 36 projected to the pixel 404 is one. In the pixel array 400, three pixels to which no X-ray absorbing layer 36 is projected and one pixel to which one X-ray absorbing layer 36 is projected are arranged alternately. Thus, the number pattern is a repetition in four pixel cycles, such as "0, 0, 0, 1, 0, 0, 0, 1, . . . ". The integrated X-ray dose received by the pixel to which one X-ray absorbing layer 36 is projected is relatively lower than that received by the pixel to which no X-ray absorbing layer 36 is projected. Thus, the pixel to which one X-ray absorbing layer 36 is projected has a relatively low output level of the voltage signal. Accordingly, the output pattern is a repetition of a pattern "high, high, high, low" in four pixel cycles, in which "high" voltage signals being in a relatively high output level continue three times and a "low" voltage signal being a low output level appears one time.

Figure 7:
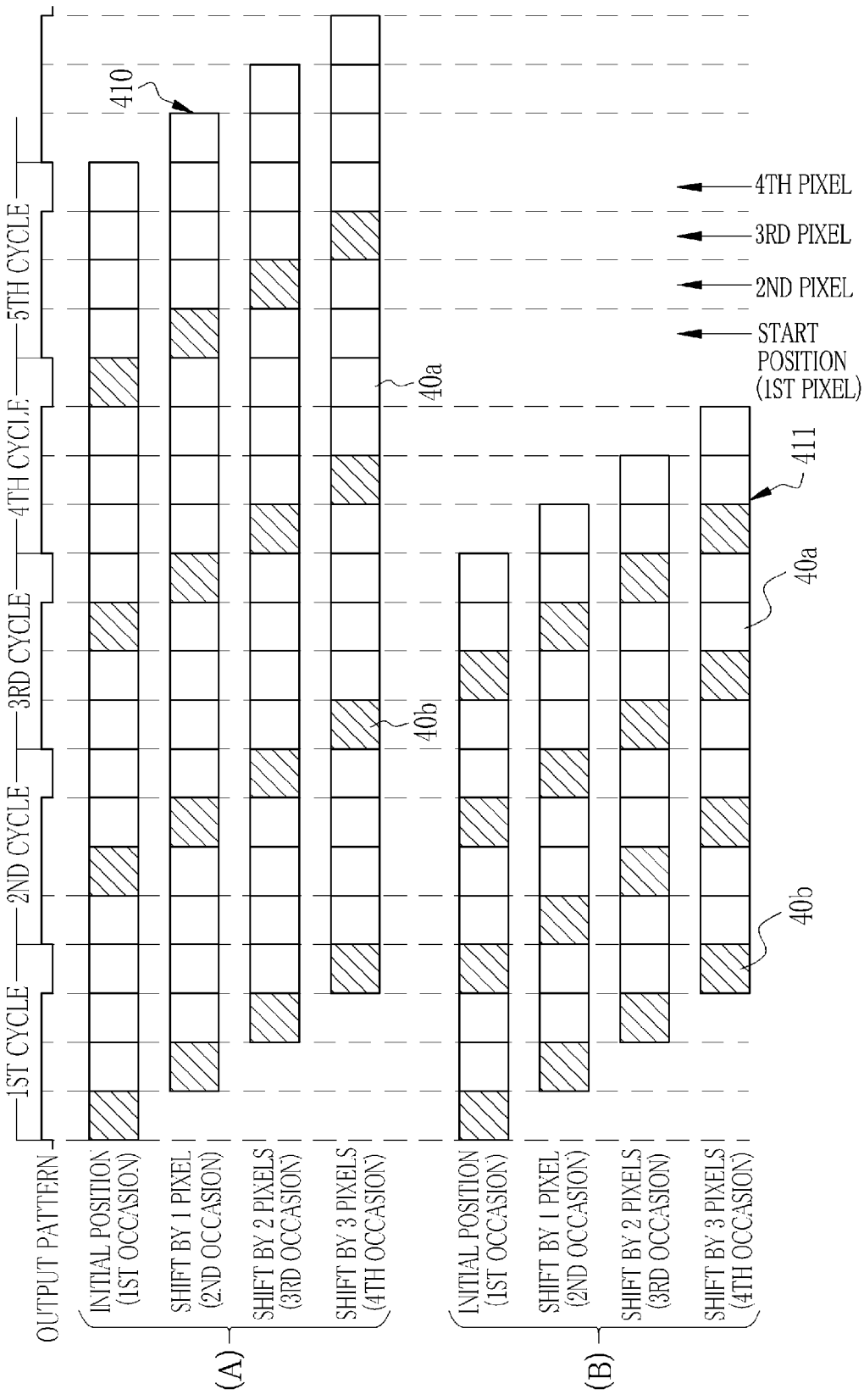
FIG. 7 is an explanatory view showing an output pattern in four pixel cycles and examples of the disposition of measurement pixels, and (A) shows the case of disposing the measurement pixels in five pixel cycles, and (B) shows the case of disposing the measurement pixels in three pixel cycles.

In the case of this output pattern, the four measurement pixels 40b are disposed in five pixel cycles as shown in a mixed pixel array 410 of FIG. 7 (A) in which the normal pixels 40a and the measurement pixels 40b are disposed in predetermined cycles. According to this disposition, although the output pattern of the four measurement pixels 40b is shifted from "high, high, high, low" to "high, high, low, high", "high, low, high, high", and "low, high, high, high" as the pixels 40 are relatively shifted from an initial position to the row direction X2 by one pixel, two pixels, and three pixels, the relation that there are three measurement pixels 40b corresponding to "high" and one measurement pixel 40b corresponding to "low" does not change. Therefore, by assigning at least these four measurement pixels 40b as a group based on which the AEC section 54 calculates the average value of the dose measurement signals, the average value is always kept invariant and the automatic exposure control is performed precisely, even if the positional relation between the electronic cassette 13 and the grid 14 is shifted.

Also, in the case of disposing the four measurement pixels 40b in three pixel cycles as shown in a mixed pixel array 411 of FIG. 7 (B), although the output pattern of the four measurement pixels 40b is shifted from "high, low, high, high" to "high, high, low, high", "high, high, high, low", and "low, high, high, high" as the pixels 40 are relatively shifted from an initial position to the row direction X2 by one pixel, two pixels, and three pixels, the relation that there are three measurement pixels 40b corresponding to "high" and one measurement pixel 40b corresponding to "low" does not change. Therefore, just as in the case of FIG. 7 (A), by assigning at least the four measurement pixels 40b disposed in the three pixel cycles as a group based on which the AEC section 54 calculates the average value of the dose measurement signals, the automatic exposure control is performed with high precision.

Figure 8:
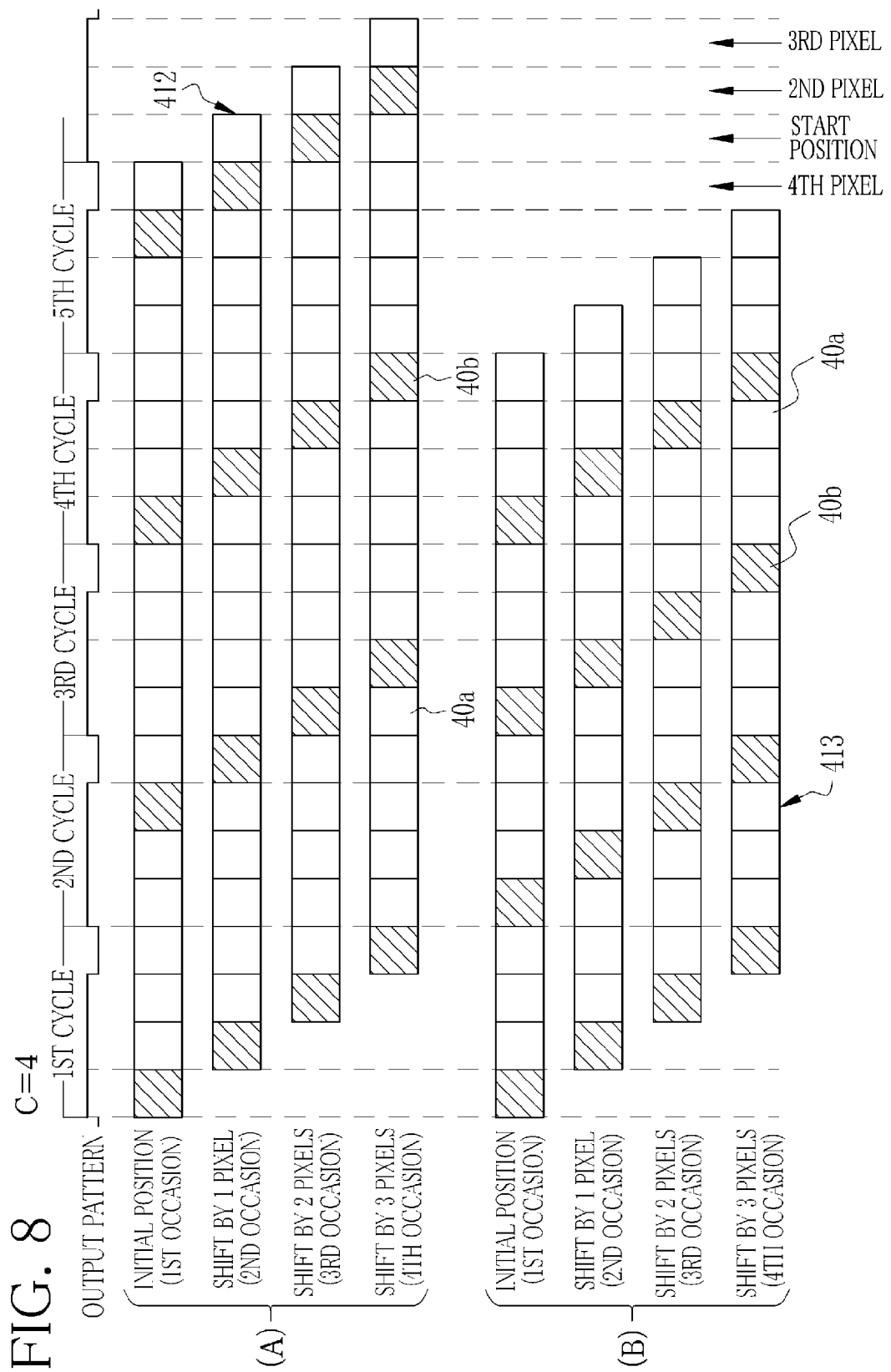
FIG. 8 is an explanatory view showing an output pattern in four pixel cycles and examples of the disposition of the measurement pixels, and (A) shows the case of disposing the measurement pixels in six pixel cycles, and (B) shows the case of disposing the measurement pixels in four pixel cycles.

However, in the case of disposing the four measurement pixels 40b in six pixel cycles as shown in a mixed pixel array 412 of FIG. 8 (A), outputs of the four measurement pixels 40b are equally "high, high, high, high" at an initial position and a relative shift of the pixels 40 in the row direction X2 by two pixels. However, the output pattern is "high, low, high, low" at a relative shift of the pixels 40 by one pixel, and the output pattern is "low, high, low, high" at a relative shift of the pixels 40 by three pixels. Thus, since the average value of the outputs of the four measurement pixels 40b varies, the precise AEC cannot be performed by assigning at least the four measurement pixels 40b disposed in the six pixel cycles as a group based on which the AEC section 54 calculates the average value of the dose measurement signals. Also in the case of a mixed pixel array 413 shown in FIG. 8 (B) in which the four measurement pixels 40b are disposed in four pixel cycles, being the same as the output pattern, outputs of the four measurement pixels 40b are equally "high, high, high, high" at an initial position and relative shifts of the pixels 40 in the row direction X2 by one pixel and two pixels. However, the output pattern is "low, low, low, low" at a relative shift of the pixels 40 by three pixels, so that the precise AEC cannot be performed just with above.

As for a pattern repeated in the output pattern, a leftmost pattern is hereinafter referred to as a first cycle. A pattern next to the leftmost pattern on the right side is referred to as a second cycle, and a pattern further next to the pattern on the right side is referred to as a third cycle. The four measurement pixels 40b in the initial position before the shift of FIG. 7 (A) are disposed in the position of the first "high" from the start position of the first cycle (leftmost) of the output pattern, the second "high" from the start position of the second cycle, the third "high" from the start position of the third cycle, and the fourth "low" from the start position of the fourth cycle. The four measurement pixels 40b in the initial position before the shift of FIG. 7 (B) are disposed in the position of the first "high" and the fourth "low" from the start position of the first cycle of the output pattern, the third "high" from the start position of the second cycle, and the second "high" from the start position of the third cycle. Although the measurement pixels 40b are disposed over a plurality of cycles, the four measurement pixels 40b are disposed evenly in the position corresponding to the first to fourth elements of the output pattern "high, high, high, low" within one cycle. On the contrary, according to FIG. 8 (A), the first two measurement pixels 40b are disposed in the position of the first and third "high", and by repetition of this, the latter two measurement pixels 40b are also disposed in the position of the first and third "high". In FIG. 8 (B), the leftmost measurement pixel 40b is disposed in the position of the first "high", and the remaining three measurement pixels 40b are also disposed in the position of the first "high" from the start position though being in different cycles.

From above consideration, it is found that the disposition of the measurement pixels 40b is preferably determined such that the four measurement pixels 40b are evenly disposed in position corresponding to each element of the output pattern "high, high, high, low" of one cycle, and the four measurement pixels 40b disposed in this manner are preferably assigned as a group of measurement pixels 40b. Thereby, the sum value or the average value of the dose measurement signals of the group of measurement pixels 40b remains invariant even if the positional relation between the grid and the measurement pixels 40b is shifted.

Note that, the above examples describe the shifts in units of one pixel, but a shift is sometimes performed by a fractional number of pixels in actual fact. For example, a shift by 0.2 pixels will be considered. Taking FIG. 7 (A) as an example, the number of the X-ray absorbing layers 36 projected to the four measurement pixels 40b is "0, 0, 0.2, 0.8", and the average value of the number of the X-ray absorbing layers 36 projected to one measurement pixel 40b is ¼, just as in the case of the shifts in units of one pixel. As a result, even if a shift amount is in units of a fractional number of pixels, the sum value or the average value of the dose measurement signals of the four measurement pixels 40b is the same as in the case of the shifts in units of one pixel.

Generalizing a condition for a disposition cycle Z of the measurement pixels 40b that makes the sum value and the average value of the group of measurement pixels 40b invariant by using symbols and the like obtains the following expression (1a).

$$Z = (R \times C) \pm 1 \qquad (1a)$$

Wherein, C represents the number of the pixels within one cycle of the output pattern (an output pattern cycle), and R is a natural number of 0 or more.

Figure 9:
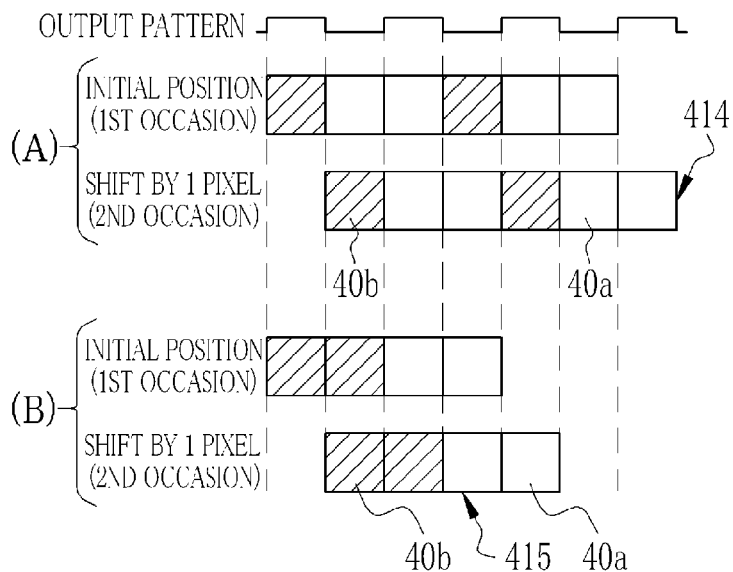
FIG. 9 is an explanatory view showing an output pattern in two pixel cycles and examples of the disposition of the measurement pixels, and (A) shows the case of disposing the measurement pixels in three pixel cycles, and (B) shows the case of disposing the measurement pixels in one pixel cycles.
Figure 10:
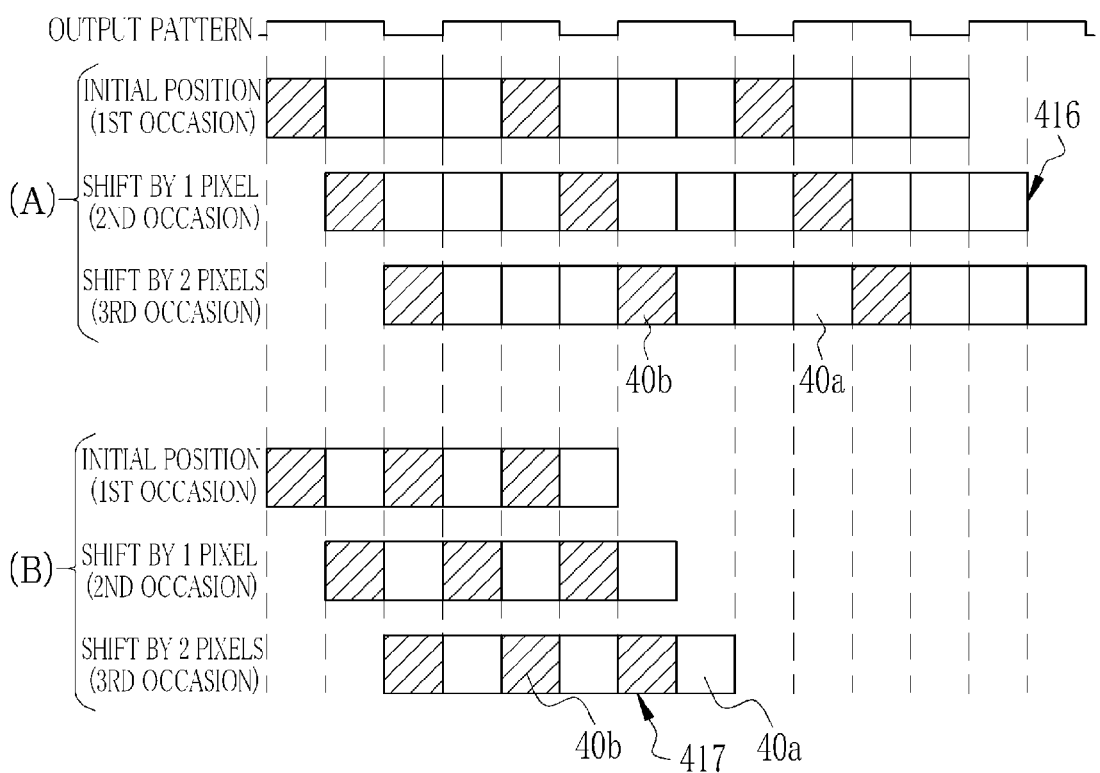
FIG. 10 is an explanatory view showing an output pattern in three pixel cycles and examples of the disposition of the measurement pixels, and (A) shows the case of disposing the measurement pixels in four pixel cycles, and (B) shows the case of disposing the measurement pixels in two pixel cycles.

The above condition holds true not only in the case of an output pattern cycle C=4, but also, for example, in the cases of C=2 of FIG. 9 and C=3 of FIG. 10, as a matter of course. In FIGS. 9 and 10, R=1 in either case. In a mixed pixel array 414 shown in FIG. 9 (A), the disposition cycle Z of the measurement pixels 40b is set at 2+1=3. In a mixed pixel array 415 shown in FIG. 9 (B), Z=2−1=1. In a mixed pixel array 416 shown in FIG. 10 (A), Z=3+1=4. In a mixed pixel array 417 shown in FIG. 10 (B), Z=3−1=2. In FIG. 9, the output pattern of the two measurement pixels 40b is "high, low" in an initial position, and "low, high" in the case of a shift of the pixels 40 relatively in the row direction X2 by one pixel, and therefore the average value of the dose measurement signals of the two measurement pixels 40b becomes the same. In FIG. 10, the output pattern of the three measurement pixels 40b takes one of "high, high, low", "high, low, high", and "low, high, high" in either of an initial position and the cases of shifts of the pixels 40 relatively in the row direction X2 by one pixel and two pixels, and hence the average value of the dose measurement signals of the three measurement pixels 40*b* becomes the same.

Here, C is represented by the following expression:

$$C = \{(1/fGN)/\Delta\} \times i$$

Wherein, fGN represents the frequency of the output pattern (the number of one-cycle output patterns per unit of length, and its reciprocal 1/fGN is the pitch of the output pattern). In the case of $2j < fG/fN \leq 2j+1$, $fGN = fG - 2jfN$. In the case of $2j+1 < fG/fN \leq 2j+2$, $fGN = (2j+2)fN - fG$. $fG = 1/G$ is a grid frequency, and $fN = 1/(2\Delta)$ is a Nyquist frequency of the pixels. "j" is an integer, and "i" is a minimum integer whose product with $(1/fGN)/\Delta$ becomes an integer. For example, if $(1/fGN)/\Delta = 7/3$, i=3.

Note that, the cycle C of the output pattern may be calculated by the above expression, or may be obtained by experiment from a stripe pattern of the X-ray image of the grid 14 that is captured by X-ray imaging without disposing the object H. Just as in the case of calculating the cycle C, in obtaining the cycle C by experiment, the disposition of the measurement pixels 40*b* is determined based on the obtained cycle C.

Standards for X-ray imaging require that variations in an exposure dose by a plurality of times of imaging of the same object H in the same imaging condition is within the range of ±5%. Thus, the average value of the X-ray doses measured by a C number of measurement pixels 40*b* is not necessarily the same at any time, and may be varied more or less as long as the variations are within the range of ±5%. Therefore, an N number of measurement pixels 40*b* that satisfy a condition of the following expression (2b) may intervene with respect to the C number of measurement pixels 40*b* composing a group based on which the AEC section 54 calculates the average value of the dose measurement signals. Wherein, "a" is a coefficient of variation that represents the difference between a pixel value of the pixel that is the most susceptible to the X-ray absorbing layers 36 and a pixel value of the pixel that is the least susceptible thereto. Now it will be considered the worst case where "a" is larger than 10%, in other words, the case of 0.1<a. For example, a=0.2 if the pixel value (a maximum value) of the pixel that is the least susceptible to the X-ray absorbing layers 36 is 20% larger than the pixel value (a minimum value) of the pixel that is the most susceptible to the X-ray absorbing layers 36.

Now, Xave represents the average value of the dose measurement signals of the C number of measurement pixels 40*b*, and it will be considered to limit the variations within the range of ±5% specified by standards, even in the case (Xmax) of disposing all of the intervening N number of measurement pixels 40*b* in the position of the pixels that are the least susceptible to the X-ray absorbing layers 36, or even in the worst case (Xmin) of disposing all of the N number of measurement pixels 40*b* in the position of the pixels that are the most susceptible to the X-ray absorbing layers 36. As long as satisfying this condition, the N number of measurement pixels 40*b* can be disposed in any position.

More specifically, the worst variation range corresponds to the subtraction of the average value of the dose measurement signals of a C+N number of measurement pixels 40*b* in disposing all the N number of measurement pixels 40*b* in the position of the pixels that are the most susceptible to the X-ray absorbing layers 36 from the average value of the dose measurement signals of the C+N number of measurement pixels 40*b* in disposing all the N number of measurement pixels 40*b* in the position of the pixels that are the least susceptible to the X-ray absorbing layers 36. This worst variation range is required to be within +10% of the average value of the dose measurement signals of the C+N number of measurement pixels 40*b* in disposing all the N number of measurement pixels 40*b* in the position of the pixels that are the least susceptible to the X-ray absorbing layers 36. This is represented by the following expression (2a). An important thing is that in each case, the average value Xave of the dose measurement signals of the C number of measurement pixels 40*b* reduces the effect of variation.

$$\frac{C \times Xave + N \times Xmax}{C + N} - \frac{C \times Xave + N \times Xmin}{C + N} \leq \frac{C \times Xave + N \times Xmin}{C + N} \times 0.1 \quad (2a)$$

Wherein, $$X\max = (1+a) \times X\min$$

Substituting $(1+a) \times X\min$ into Xmax, and calculating the expression (2a), $$\frac{a \times Xmin \times N}{C + N} \leq \frac{C \times Xave + N \times Xmin}{C + N} \times 0.1$$

Solving this expression for N brings the following expression (2b).

$$N \leq \frac{C \times Xave}{Xmin(10a - 1)} \quad (2b)$$

According to experiment of the inventors, for example, in the case of a pixel pitch $\Delta = 150$ μm and using the grid 14 of a grid pitch $G = 250$ μm (a number of the X-ray absorbing layers of 40/cm) and a grid ratio of 14:1, it is known that the difference between the pixel value of the pixel that is the most susceptible to the X-ray absorbing layers 36 and the pixel value of the pixel that is the least susceptible thereto is of the order of 20%. To determine this value of "a", for example, only the grid 14 is X-ray imaged without disposing the object H. In an area corresponding to the entirety or a region of interest of the obtained image, the pixel values of the pixels 40 extending in a direction parallel to the arrangement direction of the X-ray transparent layers 35 and the X-ray absorbing layers 36 are obtained. Then, the value of "a" may be obtained as a ratio by using the difference between a maximum value and a minimum value of the pixel values.

Note that, each of the maximum value and the minimum value of the pixel values in calculating "a" may be a value measured in a specific position, or an average of values measured in a plurality of positions. In actual fact, without any trouble of calculating the value of "a", directly substituting the maximum value and the minimum value of the pixel values, which are obtained from the image of only the grid 14 captured without disposing the object H, into Xmax and Xmin of the expression (2a) allows obtaining N. In other words, the expressions (2a) and (2b) are expressed mathematically for the sake of ease in understanding, but actually the same as calculation using the maximum value and the minimum value as is.

Note that, strictly speaking, since the grid has a manufacturing error and the like, invariant maximum and minimum values in precise cycles cannot be obtained, but a relative maximum point within one cycle may be judged as the maximum value, and a relative minimum point within one cycle may be judged as the minimum value. Otherwise, assuming the worst case, in the case of satisfying the expressions (2a) and (2b), the variations in the average value of the dose measurement signals are necessarily within the desirable range of ±5%, so that the minimum value and the maximum value may be obtained simply based on just the magnitude of numerical values in the area corresponding to the entirety or the region of interest of the obtained image, as described above. This eliminates the need for judging one cycle and facilitates easy calculation.

In the case of a pixel pitch Δ=150 μm and a grid pitch G=250 μm as described above, the output pattern cycle is five pixels. Provided that the measurement pixels 40b are disposed in position corresponding to elements of the five pixels, no X-ray absorbing layer 36 is projected to the two measurement pixels 40b, and the one X-ray absorbing layer 36 is projected to the three measurement pixels 40b, out of the five measurement pixels 40b next to each other. Since the absorptivity of one X-ray absorbing layer 36 is 20%, assuming that the pixel value of the pixel to which no X-ray absorbing layer 36 is projected is 1, the average Xave of the dose measurement signals of the five measurement pixels 40b is (1×2+0.8×3)/5=0.88. On the other hand, focusing attention on one pixel, a pixel value takes its minimum value (=0.8) if the whole one X-ray absorbing layer 36 is projected thereto, and takes its maximum value (=1) if no X-ray absorbing layer 36 is projected thereto. Thus, the difference between the maximum value and the minimum value is 0.2, and hence "a" is 0.2/0.8=0.25. Substituting this value into the expression (2b), $$N \leq \text{approximately } 3.7$$

Wherein, N becomes 3 or less, because N is an integer. In other words, if up to three measurement pixels 40b are provided in other arbitrary position additionally to the measurement pixels 40b that are provided in the position corresponding to the elements of the five pixels of the repetition cycle C, the variation range of the average value of the dose measurement signals of the C+N number of measurement pixels 40b is within the range of ±5%. Since the expression (2b) is on the assumption of the worst case, each individual dose measurement signal of the additionally provided N number of measurement pixels has a variation range less than 0.2, being a maximum variation range, in actual fact, so that the variation range is certainly smaller than ±5%. To be more specific, the average value of the dose measurement signals of a group of eight measurement pixels 40b in total, which includes five measurement pixels 40b having an average value of dose measurement signals of 0.88 and three measurement pixels 40b having a dose measurement signal of 0.8 being a minimum value, is (0.88×5+0.8×3)/8=0.85. Since none of the N number of measurement pixels 40b has a value less than the minimum value, the variation range may be within +10% of this average value. +10% of 0.85 is calculated at 0.935, and namely the average value of the C+N number of measurement pixels 40b may be within the range from 0.85 to 0.935. Relative to a case where all the dose measurement signals of the N number of measurement pixels 40b have the minimum value, the worst case is that all the dose measurement signals of the N number of measurement pixels 40b have the maximum value. In this worst case where all the N number of measurement pixels output the maximum value, the average value is calculated at 0.925, which is within the above range.

Next, the above idea will be more developed that the average value of the dose measurement signals of the C number of measurement pixels 40b is always constant as a precondition, and the variations in the average value of the dose measurement signals remain within ±5% if the N number of measurement pixels 40b, which changes the average value, are additionally provided. The variations in the average value of the dose measurement signals of the C number of measurement pixels 40b are required to remain within the range of ±5% at any time. Thus, for example, the disposition cycle Z of the measurement pixels 40b is not limited to a value calculated by the expression (1a), as long as the average value (the average value of all "high") of outputs of the four measurement pixels 40b in the initial position of FIG. 8 (A) and the case of the shift of the pixels 40 relatively to the row direction X2 by two pixels and the average value (the average value of two "high" and two "low") thereof in the cases of the shifts by one pixel and three pixels remain within ±5%.

By applying this idea to the expression (1a), the expression (1a) is further generalized into the following expression (1b):

$$Z = (R \times C) \pm D \quad (1b)$$

Wherein, D is an integer less than C, and takes such a value that in shifting at least a [C/D] number of measurement pixels 40b C occasions by one pixel, variations in the average value of the dose measurement signals of the [C/D] number of measurement pixels 40b on each occasion remain within the range of ±5% specified by standards. Parentheses of [C/D] are a gauss symbol, and [C/D] represents a maximum integer of C/D or less. For example, if C/D=5/2=2.5, [C/D]=2. In FIG. 8 (A), C=4, R=1, D=+2, and hence Z=6 and [C/D]=2. More specifically, in FIG. 8 (A), not all of the four measurement pixels 40b but two of the measurement pixels 40b compose a group, and it is required to obtain variations in the average value of the dose measurement signals in shifting this two measurement pixels 40b by four pixels. It is important to check the variations by using the [C/D] number of measurement pixels 40b and keep the variations within the range of ±5%.

$Xave_{[C/D]max}$ represents a maximum value of the average value of the dose measurement signals of the [C/D] number of measurement pixels 40b, and $Xave_{[C/D]min}$ represents a minimum value thereof. Considering in the same manner as above using these symbols, the following N may be determined. In other words, the average value of the dose measurement signals of the [C/D]+N number of measurement pixels 40b becomes its maximum value in a case where the effect of the X-ray absorbing layers 36 is alleviated by the average value $Xave_{[C/D]max}$ in disposing all the additionally provided N number of measurement pixels 40b in the position of the pixels that are the least susceptible to the X-ray absorbing layers 36. On the other hands, the average value of the dose measurement signals of the [C/D]+N number of measurement pixels 40b becomes its minimum value in a case where the effect of the X-ray absorbing layers 36 is alleviated by the average value $Xave_{[C/D]min}$ in disposing all the additionally provided N number of measurement pixels 40b in the position of the pixels that are the most susceptible to the X-ray absorbing layers 36. The difference between the maximum average value and the minimum average value is required to be within +10% of the minimum average value.

$$\frac{[C/D] \times Xave_{[C/D]max} + N \times Xmax}{[C/D] + N} - \frac{C \times Xave_{[C/D]min} + N \times Xmin}{[C/D] + N} \leq \quad (3)$$

$$\frac{[C/D] \times Xave_{[C/D]min} + N \times Xmin}{[C/D] + N} \times 0.1$$

Wherein, $Xmax = (1+a) \times Xmin$

By calculating the expression (3), the expression (2b) is generalized into the following expression (2c).

$$N \leq \frac{[C/D](11 Xave_{[C/D]min} - 10 Xave_{[C/D]max})}{Xmin(10a - 1)} \quad (2c)$$

How to concretely obtain a value of D will be explained. FIG. 11 shows output pattern variations in accordance with the number of the measurement pixels 40b contained in one group based on which the AEC section 54 calculates the average value of the dose measurement signals, and the sum value and the average value of the dose measurement signals on condition that the value of the dose measurement signal is 1 at "high" of the output pattern and 0.9 (an absorptivity of 0.1) at "low" of the output pattern. In a case where the group includes two measurement pixels 40b, there are three possible output patterns of "high, high", "high, low", and "low, low". In a case where the group includes three measurement pixels 40b, there are four possible output patterns of "high, high, high", "high, high, low", "high, low, low", and "low, low, low". In a case where the group includes four measurement pixels 40b, there are five possible output patterns of "high, high, high, high", "high, high, high, low", "high, high, low, low", "high, low, low, low" and "low, low, low, low". The average value is at its maximum "1" in a case where the output pattern has only "high". The average value decreases with increase in the number of "low", and comes to its minimum "0.9" in a case where the output pattern has only "low".

FIG. 12 shows the number of the measurement pixels 40b contained in the group based on which the AEC section 54 calculates the average value of the dose measurement signals, a combination of the maximum and minimum values of the average value that can be brought by the listed number of measurement pixels, the maximum value/the minimum value, and a judgment as to whether or not variations in the average value of the dose measurement signals of that number of measurement pixels 40b on each occasion remain within the range of ±5% specified by standards. This drawing just covers all the possible combinations of the maximum and minimum values of the average value. The judgment depends on the maximum value/minimum value. If the maximum value/the minimum value is 1.1 or less, the variations of the average value are judged to be within the range of the standards (OK). If the maximum value/the minimum value is more than 1.1, the variations of the average value are judged to be out of the range of the standards (NG). The reason why a criteria of the judgment is the maximum value/the minimum value is that the maximum value/the minimum value is stricter than the minimum value/the maximum value (taking a maximum value of 100 and a minimum value of 90 as an example, the minimum value/the maximum value=90/100=0.9 results in OK in the judgment, but the maximum value/the minimum value=100/90≅1.11 results in NG). The judgment with the stricter criteria satisfies the judgment with the looser criteria.

In a case where the group includes two measurement pixels 40b, a combination of a maximum value 1 and a minimum value 0.9 (output patterns of "high, high" and "low, low") results in NG in the judgment, while a combination of a maximum value 1 and a minimum value 0.95 (output patterns of "high, high" and "high, low") and a combination of a maximum value 0.95 and a minimum value 0.9 (output patterns of "high, low" and "low, low") result in OK in the judgment. Ina case where the group includes three or four measurement pixels 40b, only a combination of a maximum value 1 and a minimum value 0.9 (output patterns of "high, high, high" and "low, low, low", or "high, high, high, high" and "low, low, low, low") results in NG in the judgment, while the other combinations result in OK in the judgment.

Note that, by checking all of the four occasions of shifts of the measurement pixels 40b of FIG. 8 (A) by three pixels on a one-by-one basis, it is found out that the output pattern of the measurement pixels 40b of FIG. 8 (A) corresponds to the case of having a number of the measurement pixels 40b of 2, a maximum value of the average value of 1, and a minimum value of the average value of 0.95 in FIG. 12. In this case, the judgment becomes OK on the condition of an absorptivity of 0.1. Therefore, it is found out that the condition of ±5% can be satisfied not in a state of the expression (1a) with D=1, but in a state of FIG. 8 (A) with D=2.

As described above, a simulation is performed to calculate the average value with respect to variation of the output pattern relative to the number of the measurement pixels 40b based on the absorptivity, and the maximum value/the minimum value as to the combination of the maximum and minimum values of the average value, and to make the judgment based on the maximum value/the minimum value as to whether or not the variations in the average value of the dose measurement signals of the certain number of measurement pixels 40b on each occasion remain within the ±5% specified by standards. The simulation makes it possible to obtain the disposition cycle Z of the measurement pixels 40b for producing the output pattern of a combination with OK in the judgment, and D therefrom. Note that, in this example, the absorptivity is set at 0.1, and the number of combinations of the maximum value/the minimum value having OK in the judgment is reduced with increase in the absorptivity. In the case of FIG. 8 (A), a combination of a maximum value of 0.95 and a minimum value of 0.9 (output patterns of "high, low" and "low, low") does not happen on the condition that the number of the measurement pixels 40b is 2 in FIG. 12. The judgment is made on such an impossible combination for the sake of convenience in explanation, but an actual simulation is performed with excluding the impossible combination.

Figure 13A:
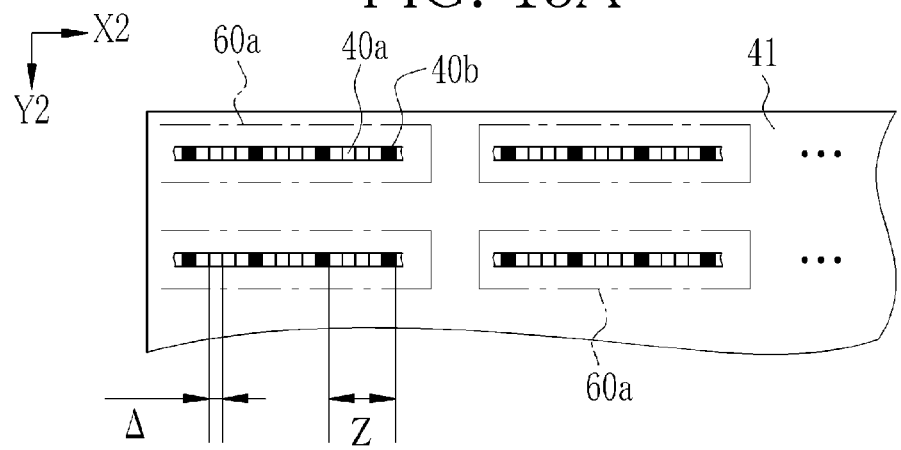
FIG. 13A is an explanatory view showing an example of a combination of mixed pixel arrays in which normal pixels and the measurement pixels are arrayed in a row direction.
Figure 13B:
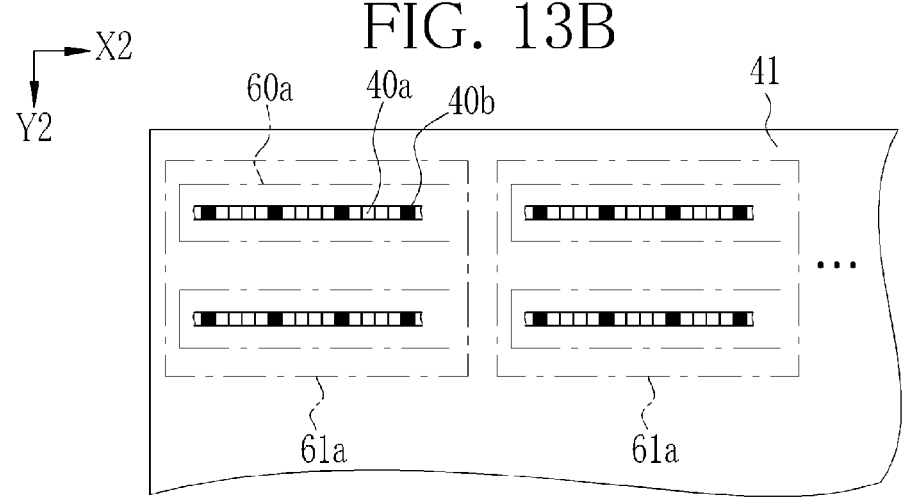
FIG. 13B is an explanatory view showing another example of a combination of the mixed pixel arrays in which the normal pixels and the measurement pixels are arrayed in the row direction.
Figure 13C:
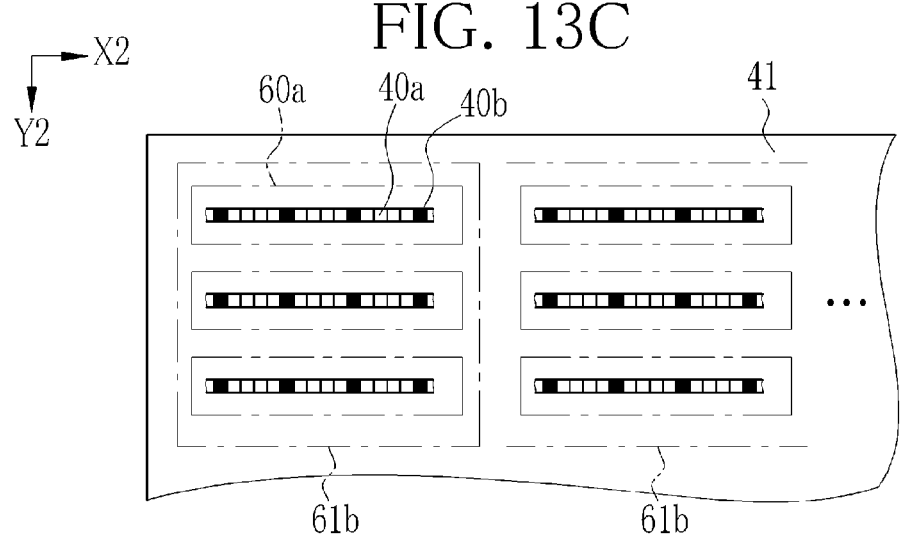
FIG. 13C is an explanatory view showing further another example of a combination of the mixed pixel arrays in which the normal pixels and the measurement pixels are arrayed in the row direction.

The above description explains about the pixels of one row for the sake of convenience in explanation, but in actual fact the X-ray dose is measured in a plurality of rows. Thus, in actual fact, as shown in FIGS. 13A to 13C, mixed pixel arrays 60a are disposed in a predetermined pattern in the imaging area 41 in which normal pixel arrays composed of only the normal pixels are arranged, such that the mixed pixel arrays 60a are substituted for the normal pixel arrays. Thus, the measurement pixels 40b are disposed in two dimensions in the imaging area 41. One or a plurality of the mixed pixel arrays 60a present within the measurement area are chosen, and the X-ray dose is measured by using the chosen mixed pixel arrays 60a. Note that, the mixed pixel arrays 60a may not be uniformly disposed over the entire imaging area 41, but may be disposed only a specific area corresponding to the measurement area set in advance, for example, left and right lung fields or the like.

As an example, in the mixed pixel array 60a shown in FIG. 13A, the four measurement pixels 40b are disposed in five pixel cycles (a cycle Z=5), and the mixed pixel arrays 60a are regularly arranged at predetermined intervals in the X2 and Y2 directions, for example. The cycle Z corresponds to the arrangement pitch of the measurement pixels 40b, and is five times as large as the pixel pitch Δ (Z=5Δ). One mixed pixel array 60a is a minimum unit used in the dose measurement, and has the four measurement pixels 40b. For the dose measurement, a block 61a having eight measurement pixels 40b composed of two mixed pixel arrays 60a as shown in FIG. 13B, or a square block 61b having twelve measurement pixels 40b composed of three mixed pixel arrays 60a as shown in FIG. 13C may be used instead. Also, the intervals between the mixed pixel arrays 60a may be irregular.

Figure 14:
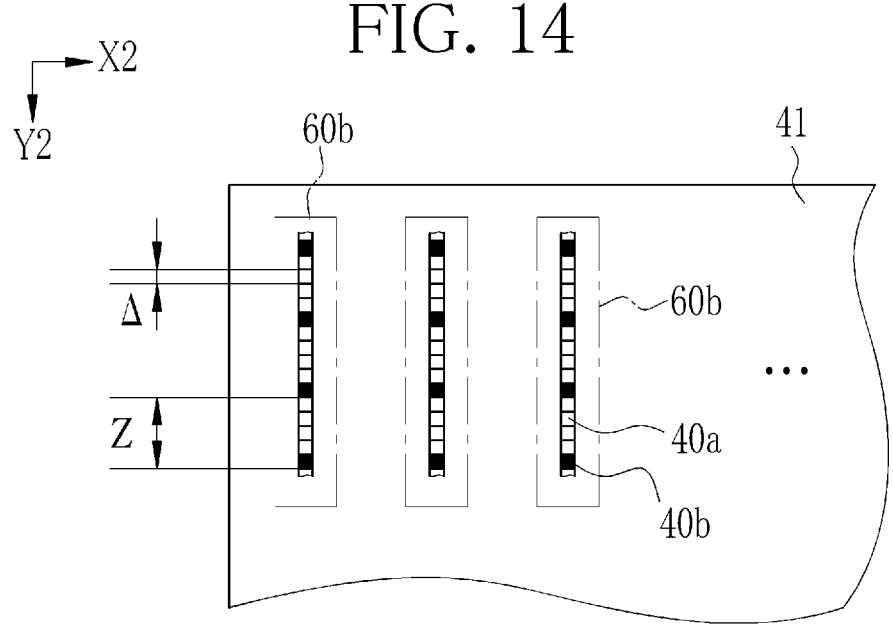
FIG. 14 is an explanatory view showing mixed pixel arrays disposed in a column direction.

The above description is based on the premise that the grid 14 is set relative to the electronic cassette 13 such that the stripes of the grid 14 extend in the column direction Y2 (such that an arrangement direction X1 of each of the X-ray transparent layers 35 and the X-ray absorbing layers 36 is in parallel with the row direction X2 of the pixels 40). However, there are cases where the electronic cassette 13 is turned 90° relative to the grid 14, and the grid 14 is set in the holder 16a such that the stripes of the grid 14 extend in the row direction X2. In this case, as shown in FIG. 14, is used the imaging area 41 formed with mixed pixel arrays 60b in which an arrangement direction of a group of measurement pixels 40b used in the dose measurement extends in the column direction Y2. In this mixed pixel array 60b, the pixel pitch Δ and the cycle Z of the measurement pixels 40b are measured in the column direction Y2.

Also, the mixed pixel arrays 60a and 60b may be mixed in the imaging area 41. For example, two mixed pixel arrays 60b are disposed between two mixed pixel arrays 60a so as to forma square. Selecting which mixed pixel arrays 60a or 60b to use in accordance with the attachment position of the grid 14 makes it possible to perform the automatic exposure control with high precision irrespective of the attachment position. Also, the automatic exposure control can be performed with high precision irrespective of the attachment position of the grid 14 by, for example, adjusting the intervals between the mixed pixel arrays 60b in the row direction X2, such that the cycle Z of the measurement pixels 40b between the mixed pixel arrays 60b in the row direction X2 coincides with the cycle Z of the measurement pixels 40b in each mixed pixel array 60b in the column direction Y2.

In each embodiment, a plurality of the measurement pixels 40b are aligned in one row or one column. However, as a mixed pixel area 60c shown in FIG. 15, a plurality of the measurement pixels 40b may be arranged in a two dimensional area with being shifted in the row direction X2 and the column direction Y2.

Figure 15:
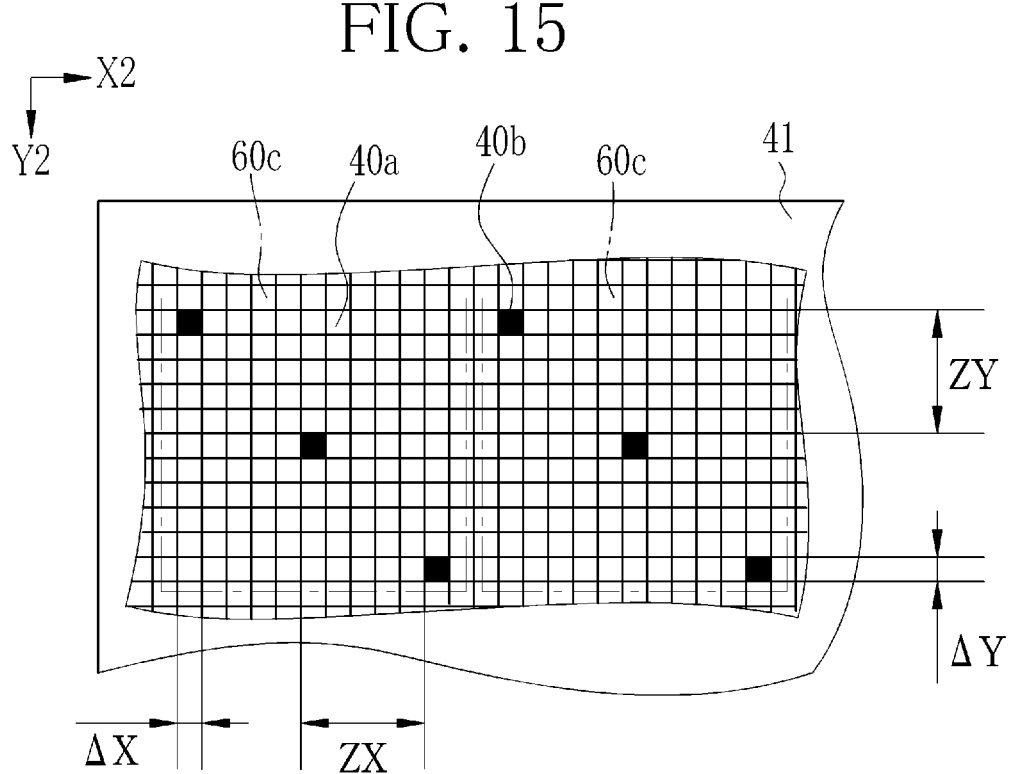
FIG. 15 is a diagram of pixel areas in which the measurement pixels are disposed in a shifted manner in the row direction and the column direction.

In the mixed pixel area 60c shown in FIG. 15, the plurality of measurement pixels 40b are arrange in different rows, and, as for the row direction X2, in five pixel cycles with leaving space of four columns. As for the row direction X2, the pixel pitch ΔX and the cycle ZX of the measurement pixels 40b in the mixed pixel area 60c are the same as the pixel pitch Δ and the cycle Z of the measurement pixels 40b in the mixed pixel array 60a shown in FIG. 13. Therefore, the average value of the dose measurement signals of a group of measurement pixels 40b in the mixed pixel area 60c is almost equal to the average value of the dose measurement signals of a group of measurement pixels 40b in the mixed pixel array 60a. Also, as for the column direction Y2, the plurality of measurement pixels 40b are disposed in five pixel cycles, though in different columns. As for the column direction Y2, the pixel pitch ΔY and the cycle ZY of the measurement pixels 40b in the mixed pixel area 60c are the same as the pixel pitch Δ and the cycle Z of the measurement pixels 40b in the mixed pixel array 60b shown in FIG. 14.

The mixed pixel area 60c is equivalent to provision of both of the mixed pixel arrays 60a and 60b, and hence facilitates performing the automatic exposure control with high precision irrespective of the attachment position of the grid 14. Furthermore, in the case of providing both of the mixed pixel arrays 60a and 60b in a mixed manner, it is necessary to select which mixed pixel arrays 60a or 60b to use in accordance with the attachment position of the grid 14. However, the mixed pixel area 60c can be used as is irrespective of the attachment position of the grid 14. Also, the use of the mixed pixel area 60c can reduce the number of the measurement pixels 40b in half, as compared with the case of providing the mixed pixel arrays 60a and 60b in a mixed manner.

In a case where the TFT and the signal line 43 are shorted out as the measurement pixel 40b described above, the electric charge of the measurement pixel 40b always flows into the signal line 43. Thus, even if the measurement pixels 40b are situated in the different rows, the electric charge of the measurement pixels 40b flows into the integrating amplifiers 46 of the signal processing circuit 45 at approximately the same time. Therefore, there is a merit that the dose measurement signals of the measurement pixels 40b in the mixed pixel area 60c can be read out at the same time.

Note that, in the mixed pixel area 60c of this example, a shift amount (five pixels) of the measurement pixels 40b is the same in the row direction X2 and the column direction Y2, but may be arbitrary changed between the row direction X2 and the column direction Y2.

In a case where a plurality of types of grids 14 are used in an exchanged manner and the condition of the disposition cycle Z differs from one grid 14 to another, the least common multiple of the disposition cycles Z is assigned as an ultimate determined disposition cycle Z. For example, in the case of using both of a grid having a condition of a disposition cycle Z=3 and a grid having a condition of a disposition cycle Z=4, the ultimate determined disposition cycle Z is 12, being the least common multiple of 3 and 4.

Since in shifting at least the [C/D] number of measurement pixels 40b C occasions by one pixel, the measurement pixels 40b are disposed in the disposition cycle Z such that the variations in the average value of the dose measurement signals of the group of measurement pixels 40b based on which the AEC section calculates the average value of the dose measurement signals on each occasion remain within ±5%, it is possible to always alleviate variation in the average value of the dose measurement signals of the group of measurement pixels irrespective of the positional relation between the electronic cassette 13 and the grid 14. Especially, provided that D=1 and the C number of measurement pixels 40b are provided, the average value of the group of measurement pixels 40b on each occasion is equalized. Therefore, it is possible to perform the automatic exposure control with high precision.

In the case of using the plurality of types of grids 14 in a switchable manner, determining the disposition cycle Z so as to satisfy all kinds of conditions can improve universality.

As factors that cause variations of an integrated radiation dose by a plurality of times of imaging in the same imaging condition, there are variations in time (synchronization time of an emission start) from transmitting the emission start signal by the emission signal I/F 25 of the source control device 11 to receiving the emission start signal by the emission signal I/F 55 of the electronic cassette 13 and starting the dose measurement by the AEC section 54, in addition to the variations in the average value of the group of measurement pixels 40*b* as described above. There are also variations in time (synchronization time of an emission stop) from transmitting the emission stop signal by the emission signal I/F 55 to receiving the emission stop signal by the emission signal I/F 25 and actually stopping the X-ray emission from the X-ray source 10 by the controller 21 of the source control device 11. Accordingly, in order to limit the variations of the integrated radiation dose by the plurality of times of imaging in the same imaging condition within the range of ±5%, including the variations in the synchronization time of the emission start and the emission stop, it is necessary to make a tolerance in the variations of the average value of the group of measurement pixels 40*b* more rigorous than ±5%, at the least. For this reason, a value by which the right side of the expression (3) is multiplied is not limited to "0.1", and the criteria of the judgment for obtaining D of the expression (1b) is not limited to ±5%. Provided that a tolerance in the variations of the average value of the group of measurement pixels 40*b* is set at ±k % (k<50), the expressions (2c) are rewritten into the following expression (2d).

$$N \leq \frac{[C/D]\{(1+k)Xave_{[C/D]min} - Xave_{[C/D]max}\}}{Xmin(a-k)} \quad (2d)$$

Note that, as a result of calculation on a certain condition, in a case where the right side of the expression (2d) is a decimal fraction less than 1, a minimum coefficient may be multiplied so as to make the decimal fraction into 1 or more, and this coefficient number of groups each of which contains a [C/N] number of measurement pixels 40*b* may be provided. For example, if N≤0.3, multiplying 0.3 by 4 results in 1.2, more than 1. In this case, four groups of the [C/N] number of measurement pixels 40*b* may be provided, and one extra measurement pixel 40*b* may be added relative thereto in other arbitrary position. This allows compliance with the tolerance of ±k %.

According to experiment of the inventors, variations in the synchronization time of the emission start and stop by wired communication are on the order of 0.5 msec in total. For example, in the case of chest imaging of an emission time of 20 msec, the variations in the integrated dose caused by the synchronization time of the emission start and stop are 0.5/20=0.025. This corresponds to 2.5%, so the tolerance in the variations of the average value of the group of measurement pixels 40*b* may be set at ±2.5% or less (k×2.5).

Note that, in a case where k is larger than 2.5 or 5, if k is less than 50, it is possible to obtain the effect of always reducing the variations in the average value of the group of measurement pixels irrespective of the positional relation between the electronic cassette 13 and the grid 14.

In the above embodiment, for the sake of convenience in explanation, provided that R=1, the measurement pixels 40*b* are disposed in the five pixel cycles as shown in FIG. 7 (A) and in the three pixel cycles as shown in FIG. 7 (B). Since the measurement pixels 40*b* are generally treated as defect pixels, the less the number of the measurement pixels 40*b* the better. It is preferable to set R at a large value and the rate of the measurement pixels 40*b* relative to all the pixels 40 at the order of approximately 0.01% (100 ppm; ppm (parts per million)=0.0001%).

Since periodicity is important in the above embodiment, is explained an example in which the grid and the pixels are in a certain positional relation (a position in which a left end of the grid and a left end of the pixel are aligned) and the X-ray absorbing layer has a certain width. There will be complementarily described a case where the left end of the grid and the left end of the pixel are misaligned or the positional relation between the grid and the pixels is not constant. For example, FIG. 10 shows a case in which a repetition of one cycle having a cycle C of the output pattern of 3 and a number pattern of "0, 0, 1". Assuming that the left end of the grid is shifted from this state to the left by 0.2 pixels, for example, the number pattern becomes "0, 0.2, 0.8, 0, 0.2, 0.8, . . . ". Thus, a cycle of "0, 0.2, 0.8" is repeated. The cycle of the number pattern is 3 pixels, and the cycle C of the output pattern is 3 pixels, just as with before the shift.

Here, as in the case of FIG. 10 (A), will be considered a case where R=1, D=1, Z=4, and the [C/D]=3 number of measurement pixels 40*b* are assigned as the group of measurement pixels 40*b*. In relatively shifting the pixels 40 in the row direction X2 by one pixel, the number pattern of the measurement pixels 40*b* is "0.2, 0.8, 0" in a shift by one pixel (second occasion), and the number pattern is "0.8, 0, 0.2" in a shift by two pixels (third occasion). In either case, the average value of the number of the X-ray absorbing layers 36 projected to one measurement pixel 40*b* is equally ⅓. As compared with the number pattern "0, 0, 1" of an initial position (first occasion) shown in FIG. 10 (A), the average value of the number of the X-ray absorbing layers 36 projected to one measurement pixel 40 is equally the same ⅓. That is to say, if the initial position is shifted by less than one pixel e.g. 0.2 pixels or the like, a measurement result remains unchanged. Furthermore, if the pixels are shifted from the initial position by less than one pixel, the measurement result is the same.

Another example will be described. In a case where the grid pitch G is four times as large as the pixel pitch Δ (G=4Δ), in a state of aligning the left end of the grid 14 and the left end of the pixel 40, the number pattern is a repetition of a cycle of "0, 0, 0, 1". Provided that R=0, D=1, Z=1, and the leftmost adjacent three pixels 40 are the measurement pixels 40*b*, the number pattern of the measurement pixels 40*b* in an initial position (first occasion) is "0, 0, 0". In a shift by one pixel (second occasion), the number pattern is "0, 0, 1". In a shift by two pixels (third occasion), the number pattern is "0, 1, 0". In a shift by three pixels (fourth occasion), the number pattern is "1, 0, 0". In the case of measuring the X-ray dose by the adjacent three measurement pixels 40*b*, the variation range of outputs of the measurement pixels 40*b* is the difference between a state where all of the three pixels output "0" in the number pattern and a state where the two pixels output "0" and the other one pixel output "1". Therefore, the average value of the number of the X-ray absorbing layers 36 projected to one measurement pixel 40*b* is 0 or ⅓.

Assuming that the left end of the grid is shifted from this state to the left by 0.2 pixels, for example, the number pattern becomes "0, 0, 0.2, 0.8, 0, 0, 0.2, 0.8, . . . ". The number pattern of the leftmost adjacent three measurement pixels 40*b* is "0, 0, 0.2" in an initial position (first occasion). The number pattern is "0, 0.2, 0.8" in a shift by one pixel (second occasion). The number pattern is "0.2, 0.8, 0" in a shift by two pixels (third occasion). The number pattern is "0.8, 0, 0" in a shift by three pixels (fourth occasion). As is apparent from above, the sum of the number of the X-ray absorbing layers 36 projected to three measurement pixels 40b does not exceed 1, so that the average of the number of the X-ray absorbing layers 36 projected to one measurement pixel 40b is between 0 and ⅓. In other words, if the initial position is shifted by a fractional number of pixels such as 0.2 pixels or the like, or the pixels are shifted by a fractional number of pixels from the initial position, variations in the average value of the number of the X-ray absorbing layers 36 projected to one measurement pixel 40b is 1 at the maximum. The position of the measurement pixels 40b may be determined in consideration of the maximum value of the variations.

In the result, considering that outputs of arbitrary two pixels vary by one X-ray absorbing layer 36, the other cases having variations of one or less correspond to a state in which the variations of one is dispersed and averaged among a plurality of the measurement pixels 40b. Therefore, the variation range of the outputs of the group of measurement pixels 40b does not become one or more. With considering a case having maximum variations, disposing or choosing the measurement pixels 40b so as to keep the variations within ±5% makes it possible to restrain the variations in the outputs of the group of measurement pixels 40b, even in a case where the initial position is shifted by a fractional number of pixels or the pixels are shifted from the initial position by a fractional number of pixels.

Note that, the grid has a manufacturing error. According to verification by the inventors, it is known that the manufacturing error of the grid is much smaller than 1%. Taking a grid having 60 X-ray absorbing layers per cm as an example, if the manufacturing error is 1%, the number of the X-ray absorbing layers is in the range of 59.4/cm to 60.6/cm. The error is minute less than 1, and hence does not have influence on the effect of reducing the variations in the integrated dose according to the present invention.

However, the manufacturing error of the grid allowed by specification is the range of ±10%. In the worst case, taking the grid having 60 X-ray absorbing layers per cm as the specification as an example, the number of the X-ray absorbing layers is in the range of 54/cm to 66/cm. Some manufacturers sell grids as long as the grids satisfy this specification as an acceptable product, and a given number of grids having a manufacturing error of 1% or more are on the market. However, in the case of using such a grid, the measurement pixels 40b should be disposed or chosen based on 60/cm, being a central value, as a matter of course, in consideration of optimization as a whole. The same goes for the case of a manufacturing error of less than 1%. As described above, referring to the central value of the range of the variations in the number of the X-ray absorbing layers due to the manufacturing error of the grid brings the large effect of reducing the variations in the integrated dose. Also, each grid to be used may be X-ray imaged without disposing any object, and the actual number of the X-ray absorbing layers may be obtained from the captured image to dispose or choose the measurement pixels 40b based on the actual number.

The above embodiment describes the examples in which the grid and the measurement pixels are relatively shifted in a direction in parallel with the arrangement direction X1 of the X-ray transparent layers and the X-ray absorbing layers. One reason of this is in setting the electronic cassette in the holder of the imaging stand or the imaging table, the electronic cassette being a rectangle in shape is often caught from above and below i.e. two directions for fixing. In such a state, the electronic cassette is not shifted in the Y1 direction, but tends to be shifted in the X1 direction because there is provided a certain amount of play in the X1 direction. On the contrary, in a state where the electronic cassette is fixed in the X1 direction and shiftable in the Y1 direction, no measurement error caused by the positional shift between the electronic cassette and the grid is produced.

As another case, a state in which there is more or less play in both of the X1 direction and the Y1 direction will be considered. In this case, the grid is sometimes inclined more or less relative to the pixels. The inclination of less than 90° relative to the pixels causes that the grid pitch appears to become large. For example, in the case of the grid having the number of the X-ray absorbing layers of 60/cm, the grid pitch G is approximately 167 µm. If this grid is inclined 10°, the grid pitch G comes to be 167/cos 10°=approximately 170 µm (the number of the X-ray absorbing layers of approximately 59/cm). Provided that θ represents an inclination angle, the grid pitch G appears to be 1/cos θ times larger than a value without having the inclination. If θ=10°, 1/cos θ=approximately 1.02. Even if there is play in both of the X1 direction and the Y1 direction, it is impossible in actual fact to use the grid in a state of being inclined by 10° relative to the pixels. Even if the grid is inclined 10° relative to the pixels, this is an error of the order of ±2% at the maximum. This is less than the above-described manufacturing error ±10% of the grid in general, and hence has little effect. Thus, the certain amount of inclination of the grid relative to the pixels causes no problem, if the positions of the measurement pixels 40b are determined based on the central value, as described in the description of the manufacturing error of the grid.

Since the grid 14 is attached the housing 31 of the electronic cassette 13 or the holder 16a of the imaging stand 16, there is a distance of at least the thickness of the housing 31 between the grid 14 and the imaging area 41. Therefore, a projection image of the grid 14 to the imaging area 41 is actually enlarged as compared in the case of contacting the grid 14 and the imaging area 41. In the above embodiment, the expression for calculating the cycle C of the output pattern does not consider the distance between the grid 14 and the imaging area 41. However, since the distance between the grid 14 and the imaging area 41 is much smaller than the distance (SID; source image distance) between the focal point 10a and the imaging area 41, an enlargement factor of the projection image of the grid 14 to the imaging area 41 is slight as compared to the case of contacting the grid 14 and the imaging area 41. Thus, there is no problem if the distance between the grid 14 and the imaging area 41 is not considered in the expression calculating the cycle C of the output pattern. As a matter of course, for the sake of better precision, the cycle C of the output pattern may be calculated by an expression with consideration given to the distance between the grid 14 and the imaging area 41. Note that, in the case of obtaining the cycle C by experiment from a fringe pattern of an X-ray image of the grid 14 that is captured without disposing the object H, the distance between the grid 14 and the imaging area 41 is reflected in the fringe pattern of the X-ray image, so there is no need for giving attention to the distance between the grid 14 and the imaging area 41.

Figure 16:
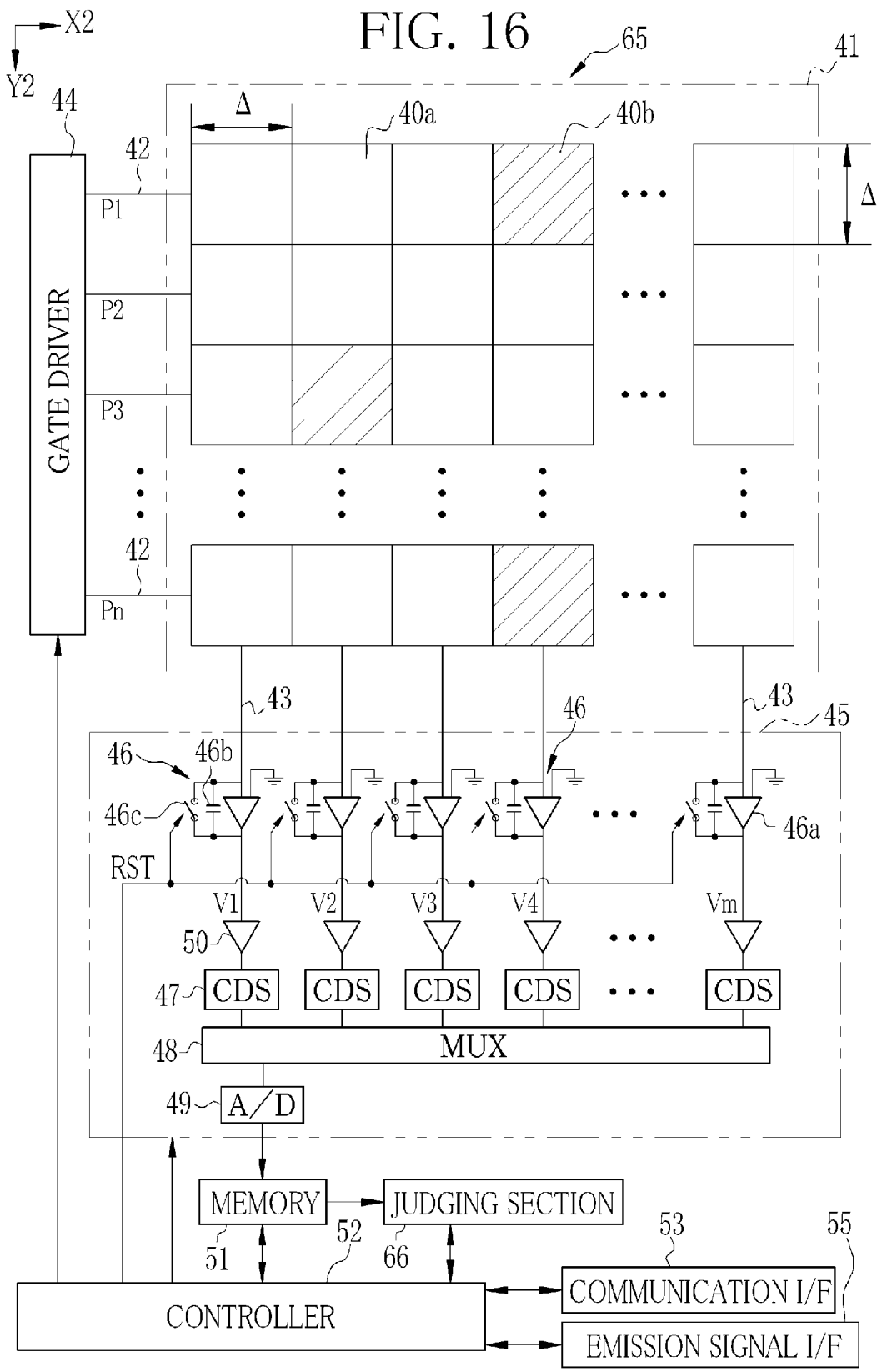
FIG. 16 is a block diagram of an electronic cassette that detects the start of X-ray emission.

Some X-ray imaging systems do not have a communication function between the source control device 11 and the electronic cassette 13. In this case, the emission start signal is not transmitted to the source control device 11 and the electronic cassette 13. In the X-ray imaging system without having the communication function, as shown in FIG. 16, an image detector 65 is provided with an emission start judging section (hereinafter called judging section) 66. This judging section 66 stores an emission start threshold value, and judges the moment of starting the X-ray emission by comparison between a measurement value and the threshold value. Also, the emission time of the X-rays is inputted from the console 15 based on the contents of the examination order. This emission time is transmitted to the electronic cassette 13. Note that, no AEC section 54 is provided for lack of the communication function between the source control device 11 and the electronic cassette 13.

During standby for X-ray imaging, the integrating amplifiers 46 are reset in relatively short cycles, and the measurement of the X-ray dose is repeatedly carried out by using the group of measurement pixels 40b. The measurement value of each measurement pixel 40b measured each time is sent to the memory 51. Since this embodiment aims at detecting the X-ray emission, the measurement value of previous time is updated with the measurement value of this time in the memory 51. Upon updating the memory 51 with the new measurement values, the judging section 66 reads out the measurement values of the group of measurement pixels 40b present in the irradiation field or all the measurement pixels present in the irradiation field, and calculates the average value thereof. Note that, it is preferable to choose only the measurement pixels 40b that are present in a directly exposed area on which the X-rays are directly applied without passing through the object in the imaging area, and judge the emission start with the use of the chosen measurement pixels 40b. Instead of the measurement pixels 40b, a specific dose measurement sensor group may be disposed in the directly exposed area.

The judging section 66 judges the start of the X-ray emission at the instant when the average value exceeds the emission start threshold value. In a case where the judging section 66 judges the start of the X-ray emission, the controller 52 shifts the operation of the image detector 65 from the reset operation to the accumulation operation, to detect the X-ray image by the normal pixels 40a as described above. The controller 52 measures an elapsed time from the start of the X-ray emission, and ends the accumulation operation after a lapse of the X-ray emission time set in the console 15. After the completion of the X-ray imaging, the X-ray image is read out of the electronic cassette 13, as described above.

In the imaging using the grid, the grid 14 is disposed in front of the electronic cassette 13. Disposing the measurement pixels 40b based on the above conditions eliminates the effect of the positional shift that occurs between the electronic cassette 13 and the grid 14. Accordingly, the electronic cassette 13 can precisely detect the start of the X-ray emission, and detect the X-ray image by the image detector 65.

According to each of the above embodiments, as shown in FIG. 5, the normal pixels 40a and the measurement pixel 40b are connected to the same signal line 43. Since the measurement pixels 40b become the defect pixels, the number of the measurement pixels is much smaller than that of the normal pixels 40a. A slight amount of leak current flows from the normal pixel 40a even in an off state of the TFT. The number of the normal pixels 40a is much larger than that of the measurement pixels, so there is a problem that addition of electric charge based on the leak current of the normal pixels 41a to the electric charge of the measurement pixels 40b greatly affects the dose measurement signals as noise. Therefore, it is preferable that a column (a column outputting the voltage signal V1 or V3 of FIG. 5) having no measurement pixel 40b be provided next to a column (for example, a column outputting the voltage signal V2 of FIG. 5) having the measurement pixel 40b, and in sampling the dose measurement signal by the AEC section 54, an output of the column having no measurement pixel 40b is subtracted from an output of the column having the measurement pixel 40b in order to eliminate the effect of the electric charge caused by the leak current and take out only an output based on the electric charge from the measurement pixel 40b. For this reason, it is preferable that at least the one normal pixel 40a be disposed between the two measurement pixels 40b as shown in FIG. 7 (A) and the like, rather than disposing the measurement pixels 40b in a row as shown in FIG. 9 (B).

As the pixels 40, pixels specific to the normal pixels 40a and pixels (dual function pixels) changeable into the measurement pixels 40b may be prepared. This dual function pixel can be actualized by adding another TFT, which is different from the TFT for image reading, to the normal pixel 40a. Information about the disposition cycles Z of the group of measurement pixels 40, which are in accordance with the grids 14 to be used, is stored in associated with the imaging condition, and the double function pixels are changed into the measurement pixels 40b in accordance with the imaging condition. Otherwise, an image of the grid 14 that is obtained by X-ray imaging without disposing the object H may be analyzed, and the disposition cycle Z may be calculated based on obtained information about the cycle C of the output pattern to determine which ones of the dual function pixels are changed into the measurement pixels 40b.

A sufficient number of the dual function pixels are preferably provided in the image detector 30. A dose measurement value is taken from every dual function pixel to the memory 51. The AEC section 54 selects the dose measurement values based on the disposition cycle Z. It is essential only that the information about the disposition cycle Z be obtained to select the dual function pixels to be used as the measurement pixels 40b in real time during X-ray imaging.

According to the above embodiments, in the measurement pixel 40b, the source electrode and the drain electrode of the TFT for readout driven by the gate driver 44 is shorted out. Instead of shorting the TFT for readout, every pixel 40 may be provided with another TFT for measurement. While the TFT for readout is turned off in the accumulation operation, the TFT for measurement may be selectively turned on to make the electric charge produced in the pixel 40 flow into the capacitor 46b of the integrating amplifier 46. The pixel 40 whose TFT for measurement is selectively turned on is used as the measurement pixel 40b. Thereby, in the case of selectively using a plurality of types of grids 14, it is possible to change the normal pixel 40a into the measurement pixel 40b in accordance with the type of each grid 14. In this case, position data of each grid 14 is stored in a memory. The controller 52 reads out the position data corresponding to the grid to be used. Then, a specific gate driver is driven to turn on the TFTs for measurement of the measurement pixels 40b designated by the position data in predetermined cycles. Thereby, accumulated electric charge is read out once every predetermined time and the X-ray dose per unit of time is measured.

Also, with taking advantage of the fact that an electric current that is based on electric charge produced in a pixel flows through the bias line for supplying the bias voltage to each pixel, an electric current flowing through the bias line connected to a specific pixel may be sampled to detect the X-ray dose. In this case, the pixel whose electric current flowing through the bias line is sampled is designated as the measurement pixel. In a like manner, a leak current flowing from a pixel may be sampled to detect the dose. Also in this case, the pixel whose leak current is sampled is designated as the measurement pixel.

In the above embodiment, the pixels 40 are disposed at the predetermined pitch Δ in two dimensions in the imaging area. Parts of the pixels 40 are designated as the measurement pixels 40b, and the others are designated as the normal pixels 40a. The normal pixels 40a and the measurement pixels 40b are of the same size. Note that, the measurement pixel 40b may be larger or smaller than the normal pixel 40a in size. Also, slim dose measurement sensors extending in the X2 or Y2 direction may be disposed between columns or rows of the normal pixels 40a so as to satisfy the above conditions. However, the length of the dose measurement sensor is made shorter than a row of the ten pixels 40, so that the defect correction is effective at making the dose measurement sensor inconspicuous.

The TFT type image detector is described as an example in the above embodiments, but a CMOS (complementary metal oxide semiconductor) type image detector may be used instead. Also, the present invention is not limited to the electronic cassette being a portable type X-ray image detecting device, and may be applied to an integral type X-ray image detecting device attached to the imaging stand or the imaging table. Furthermore, the present invention is applicable to the case of capturing another type of radiation such as γ-rays, instead of the X-rays.

The present invention is not limited to the embodiments described above, and the embodiments can be combined within the scope of configurations described in the embodiments.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. A radiation image detecting device having an image detector formed with an imaging area, and said radiation image detecting device being used together with a grid capable of being disposed in front of said image detector, said radiation image detecting device comprising:
said grid having strip-shaped radiation transparent layers and radiation absorbing layers extending in a first direction to remove scattered rays produced upon radiation passing through an object, a plurality of said radiation transparent layers and said radiation absorbing layers being formed alternatingly at a grid pitch, G, in a second direction orthogonal to said first direction;
said imaging area being provided with a plurality of pixels arrayed in said second direction at a pixel pitch Δ and a plurality of dose measurement sensors, said plurality of pixels accumulating electric charge in accordance with a received radiation dose in a readable manner to detect a radiographic image of said object, said plurality of dose measurement sensors measuring said received radiation dose; and
in at least a group of dose measurement sensors out of said plurality of dose measurement sensors, a [C/D] number of dose measurement sensors being disposed or chosen in the following cycle Z:
condition:

$$Z = (R \times C) \pm D$$

wherein,
C represents a cycle of a repetition pattern appearing in said second direction in a radiographic image of said grid, and is represented in units of the number of said pixels,
R represents a natural number of 0 or more,
D represents an integer less than said cycle C, and
[C/D] represents a maximum integer equal to or less than C/D.

2. The radiation image detecting device according to claim 1, further comprising:
a judging section for judging an emission state of said radiation based on a measurement value of said group of dose measurement sensors; and
a controller for performing control in accordance with a judgment result of said judging section.

3. The radiation image detecting device according to claim 2, wherein said pixels include a normal pixel for detecting said radiographic image and a measurement pixel of the same size as said normal pixel and used as said dose measurement sensor, and said normal pixel and said measurement pixel are disposed in said first and second directions in two dimensions in a mixed manner.

4. The radiation image detecting device according to claim 3, wherein said normal pixel and said measurement pixel are connected to a common signal processing circuit, and electric charge of said normal pixel is accumulated and electric charge of said measurement pixel is read out to said signal processing circuit during emission of said radiation.

5. The radiation image detecting device according to claim 3, wherein provided that at least said [C/D] number of measurement pixels are shifted C occasions by one pixel, D takes such a value that variations in output values of said [C/D] number of measurement pixels on each occasion are within the range of ±k % (k<50).

6. The radiation image detecting device according to claim 5, wherein said value of D is determined by judging whether or not said variations in said output values on each occasion remain within said range of ±k % with reference to a minimum value of said output values on each occasion.

7. The radiation image detecting device according to claim 3, wherein said group of measurement pixels allow the existence of an N number of measurement pixels satisfying the following conditional expression, in addition to said [C/D] number of measurement pixels:
conditional expression:

$$N \le \frac{[C/D]\{(1+k)Xave_{[C/D]min} - Xave_{[C/D]max}\}}{Xmin(a-k)}$$

wherein,
$Xave_{[C/D]min}$ represents a minimum value of an average value of outputs of said [C/D] number of measurement pixels,
$Xave_{[C/D]max}$ represents a maximum value of said average value of said outputs of said [C/D] number of measurement pixels,
Xmin represents an output in a case where said N number of measurement pixels are disposed in the position of said pixels that are least susceptible to said radiation absorbing layers, and
"a" represents a coefficient of variation representing the difference between a pixel value of said pixel that is the most susceptible to said radiation absorbing layer and a pixel value of said pixel that is the least susceptible to said radiation absorbing layer.

8. The radiation image detecting device according to claim 5, wherein D=1 so that said output value on each occasion is invariable.

9. The radiation image detecting device according to claim 5, wherein k≤5.

10. The radiation image detecting device according to claim 5, wherein k≤2.5.

11. The radiation image detecting device according to claim 3, wherein in the case of selectively using a plurality of said grids having different conditions of a disposition cycle Z of said group of measurement pixels, a least common multiple of a plurality of said disposition cycles Z is used as a disposition cycle Z sharable among said plurality of grids.

12. The radiation image detecting device according to claim 3, wherein in automatic exposure control, said judging section judges whether or not a total radiation dose being an integrated value of a radiation dose measured by each of said measurement pixels or an average value of said total radiation doses has reached a target dose, and stops emission of said radiation in a case where said total radiation dose or said average value is judged to have reached said target dose.

13. The radiation image detecting device according to claim 3, wherein the decision of the position of said group of measurement pixels stipulated in said second direction is also applied to said first direction.

14. The radiation image detecting device according to claim 3, wherein said image detector is an electronic cassette contained in a portable housing.

15. A radiation imaging system comprising:
 (A) a radiation source for applying radiation to an object;
 (B) a source control device for controlling the operation of said radiation source; and
 (C) a radiation image detecting device having an image detector formed with an imaging area, and said radiation image detecting device being used together with a grid capable of being disposed in front of said image detector, said radiation image detecting device including:
 said grid having strip-shaped radiation transparent layers and radiation absorbing layers extending in a first direction to remove scattered rays produced upon radiation passing through an object, a plurality of said radiation transparent layers and said radiation absorbing layers being formed at a grid pitch G alternately in a second direction orthogonal to said first direction;
 said imaging area being provided with a plurality of pixels arrayed in said second direction at a pixel pitch Δ and a plurality of dose measurement sensors, said plurality of pixels accumulating electric charge in accordance with a received radiation dose in a readable manner to detect a radiographic image of said object, said plurality of dose measurement sensors measuring said received radiation dose; and
 in at least a group of dose measurement sensors out of said plurality of dose measurement sensors, a [C/D] number of dose measurement sensors being disposed or chosen in the following cycle Z:
 condition:

$Z=(R \times C) \pm D$ wherein,
 C represents a cycle of a repetition pattern appearing in said second direction in a radiographic image of said grid, and is represented in units of the number of said pixels,
 R represents a natural number of 0 or more,
 D represents an integer less than said cycle C, and
 [C/D] represents a maximum integer equal to or less than C/D.

16. An operation method of a radiation imaging system including:
 (A) a radiation source for applying radiation to an object;
 (B) a source control device for controlling the operation of said radiation source; and
 (C) a radiation image detecting device having an image detector formed with an imaging area, and said radiation image detecting device being used together with a grid capable of being disposed in front of said image detector, said radiation image detecting device including:
 said grid having strip-shaped radiation transparent layers and radiation absorbing layers extending in a first direction to remove scattered rays produced upon radiation passing through an object, a plurality of said radiation transparent layers and said radiation absorbing layers being formed at a grid pitch G alternately in a second direction orthogonal to said first direction;
 said imaging area being provided with a plurality of pixels arrayed in said second direction at a pixel pitch Δ and a plurality of dose measurement sensors, said plurality of pixels accumulating electric charge in accordance with a received radiation dose in a readable manner to detect a radiographic image of said object, said plurality of dose measurement sensors measuring said received radiation dose; and
 in at least a group of dose measurement sensors out of said plurality of dose measurement sensors, a [C/D] number of dose measurement sensors being disposed or chosen in the following cycle Z:
 condition:

$Z=(R \times C) \pm D$ wherein,
 C represents a cycle of a repetition pattern appearing in said second direction in a radiographic image of said grid, and is represented in units of the number of said pixels,
 R represents a natural number of 0 or more,
 D represents an integer less than said cycle C, and
 [C/D] represents a maximum integer equal to or less than C/D;
 said operation method comprising the steps of:
 (i) measuring a radiation dose by at least said group of dose measurement sensors out of said plurality of dose measurement sensors;
 (ii) judging whether or not a total radiation dose being an integrated value of each of said radiation doses measured by said group of dose measurement sensors or an average value of said total radiation doses has reached a target dose; and
 (iii) stopping the operation of said radiation source to stop emission of said radiation, at the instant when said total radiation dose or said average value reaches said target dose.

* * * * *